United States Patent
Cross et al.

(10) Patent No.: US 9,579,470 B2
(45) Date of Patent: Feb. 28, 2017

(54) DEDICATED NEEDLE ASSEMBLY

(75) Inventors: John David Cross, Long Buckby (GB); Malcolm Stanley Boyd, Wellesbourne (GB); Daniel Thomas De Sausmarez Lintell, Rugby (GB); Alasdair George Young, San Francisco, CA (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/635,870

(22) PCT Filed: Mar. 23, 2011

(86) PCT No.: PCT/EP2011/054418
§ 371 (c)(1),
(2), (4) Date: Mar. 21, 2013

(87) PCT Pub. No.: WO2011/117282
PCT Pub. Date: Sep. 29, 2011

(65) Prior Publication Data
US 2013/0231614 A1 Sep. 5, 2013

Related U.S. Application Data

(60) Provisional application No. 61/317,856, filed on Mar. 26, 2010.

(30) Foreign Application Priority Data

Jul. 21, 2010 (EP) .................................. 10170280

(51) Int. Cl.
*A61M 5/34* (2006.01)
*A61M 5/31* (2006.01)
(Continued)

(52) U.S. Cl.
CPC ............ *A61M 5/34* (2013.01); *A61M 5/3134* (2013.01); *A61M 5/326* (2013.01);
(Continued)

(58) Field of Classification Search
CPC ...... A61M 5/2455; A61M 5/284; A61M 5/24; A61M 5/2448; A61M 5/3134;
(Continued)

(56) References Cited

U.S. PATENT DOCUMENTS 3,055,364 A * 9/1962 Myerson et al. ............. 604/192
3,563,240 A 2/1971 Silver
(Continued)

FOREIGN PATENT DOCUMENTS

| EP | 0144483 A2 | 6/1985 |
|---|---|---|
| JP | 2006512106 A | 4/2006 |

(Continued)

OTHER PUBLICATIONS

English Language Translation of EP 0 144 483.
(Continued)

*Primary Examiner* — Kami A Bosworth
(74) *Attorney, Agent, or Firm* — McDonnell Boehnen Hulbert & Berghoff LLP

(57) ABSTRACT

A dedicated needle assembly (300) that can be attached only to a dedicated drug delivery device (400) is disclosed. The dedicated needle assembly (300) comprises a connecting body (320) extending from a distal end to a proximal end. A dedicated mechanical coupling (310) is configured at the proximal end of the connecting body (320). The dedicated mechanical coupling (310) forms a releasable connection to a distal end of the dedicated drug delivery device (400). The dedicated needle assembly (300) may comprise a medicated module or, alternatively, a non-medicated module. In one
(Continued)

arrangement, the dedicated mechanical coupling (310) is integral with the dedicated needle assembly (300).

11 Claims, 15 Drawing Sheets

(51) Int. Cl.
| | |
|---|---|
| *A61M 5/24* | (2006.01) |
| *A61M 5/315* | (2006.01) |
| *A61M 5/32* | (2006.01) |
| *A61M 5/50* | (2006.01) |

(52) U.S. Cl.
CPC ........ *A61M 5/3243* (2013.01); *A61M 5/3294* (2013.01); *A61M 5/347* (2013.01); *A61M 5/348* (2013.01); *A61M 5/24* (2013.01); *A61M 5/2455* (2013.01); *A61M 5/31551* (2013.01); *A61M 5/31593* (2013.01); *A61M 5/321* (2013.01); *A61M 5/3297* (2013.01); *A61M 5/50* (2013.01); *A61M 2005/2407* (2013.01); *A61M 2005/3142* (2013.01); *A61M 2005/3247* (2013.01); *A61M 2005/3267* (2013.01); *A61M 2205/6045* (2013.01)

(58) Field of Classification Search
CPC ...... A61M 5/3294; A61M 5/34; A61M 5/347; A61M 5/348; A61M 2005/2407; A61M 2005/2451; A61M 2005/2485; A61M 2005/2488; A61M 2005/2492; A61M 5/31593; A61M 5/31595; A61M 5/3243; A61M 5/326; A61M 5/3297; A61M 5/50; A61M 5/321; A61M 2005/3142; A61M 2005/3247; A61M 2005/3267
USPC ........ 604/240–243, 200–203, 192, 193, 205, 604/86, 88
See application file for complete search history.

(56) References Cited

U.S. PATENT DOCUMENTS

| | | | | |
|---|---|---|---|---|
| 4,581,016 | A * | 4/1986 | Gettig | 604/88 |
| 5,069,225 | A * | 12/1991 | Okamura | 600/578 |
| 5,281,198 | A * | 1/1994 | Haber et al. | 604/86 |
| 5,531,683 | A * | 7/1996 | Kriesel | A61M 5/2429 604/416 |
| 6,562,002 | B1 * | 5/2003 | Taylor | A61M 5/282 604/82 |
| 7,645,264 | B2 * | 1/2010 | Marsh et al. | 604/117 |
| 7,985,216 | B2 * | 7/2011 | Daily et al. | 604/533 |
| 2002/0004648 | A1 * | 1/2002 | Larsen et al. | 604/195 |
| 2004/0015128 | A1 * | 1/2004 | Taylor | 604/92 |
| 2004/0054336 | A1 * | 3/2004 | Klint et al. | 604/272 |
| 2006/0229562 | A1 * | 10/2006 | Marsh | A61M 5/204 604/164.01 |
| 2008/0177238 | A1 * | 7/2008 | Follman et al. | 604/263 |
| 2009/0270814 | A1 | 10/2009 | Masi et al. | |
| 2009/0318859 | A1 * | 12/2009 | Eichhorst et al. | 604/68 |
| 2010/0152669 | A1 * | 6/2010 | Rosenquist | 604/192 |
| 2011/0160676 | A1 * | 6/2011 | Liversidge | 604/198 |
| 2012/0109052 | A1 * | 5/2012 | Wei et al. | 604/82 |
| 2012/0123346 | A1 * | 5/2012 | Davies et al. | 604/191 |
| 2012/0226238 | A1 * | 9/2012 | Davies et al. | 604/191 |
| 2013/0116617 | A1 * | 5/2013 | Martin et al. | 604/82 |

FOREIGN PATENT DOCUMENTS

| | | |
|---|---|---|
| WO | 2004004812 A1 | 1/2004 |
| WO | 2009150078 A1 | 12/2009 |

OTHER PUBLICATIONS

International Preliminary Report on Patentability for Int. App. No. PCT/EP2011/054418, mailed Oct. 11, 2012.
English Language of Notice of Reasons for Rejection for Japanese Patent Application No. 2013-500485 dated Jan. 6, 2015.

* cited by examiner

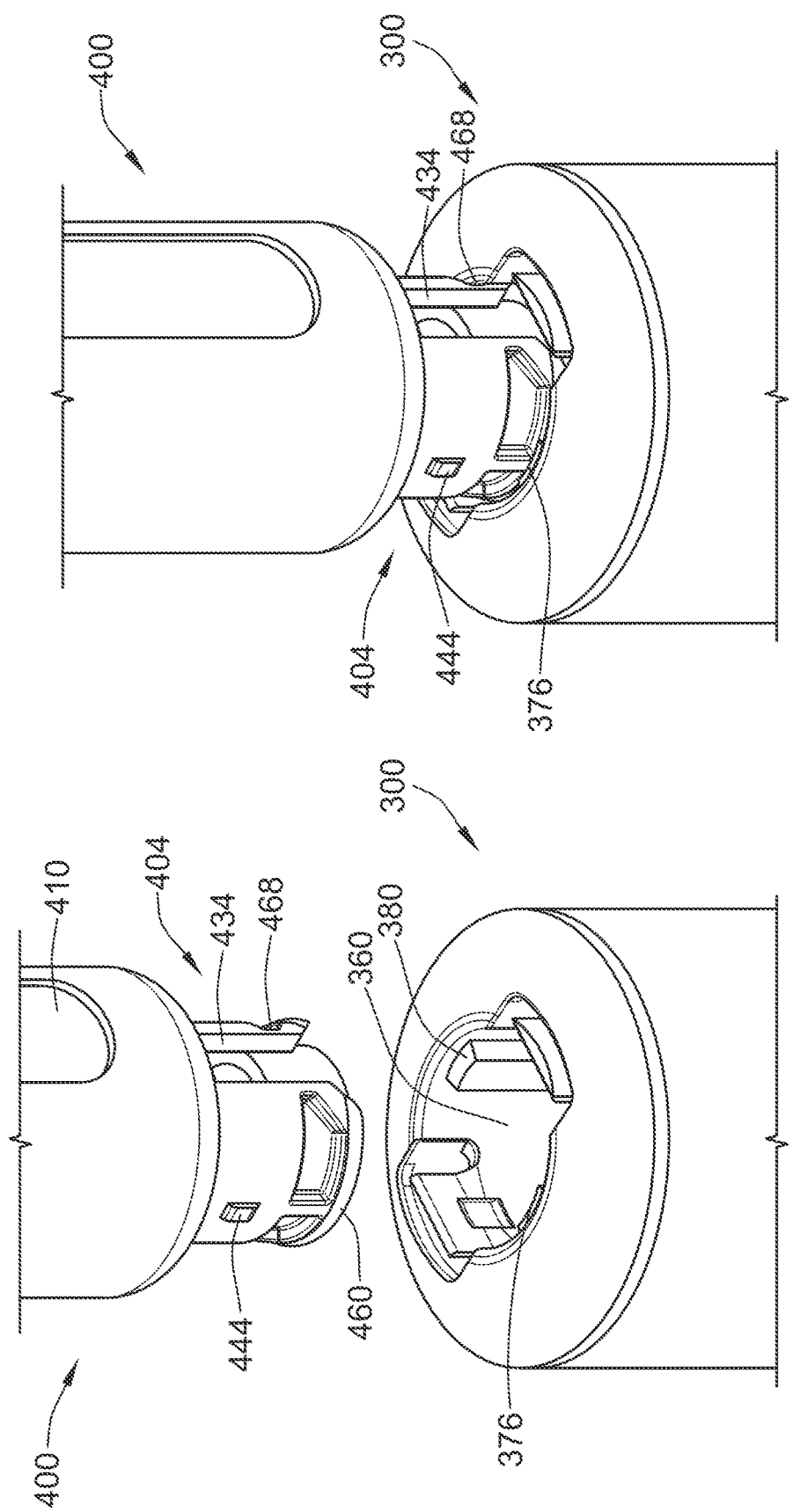

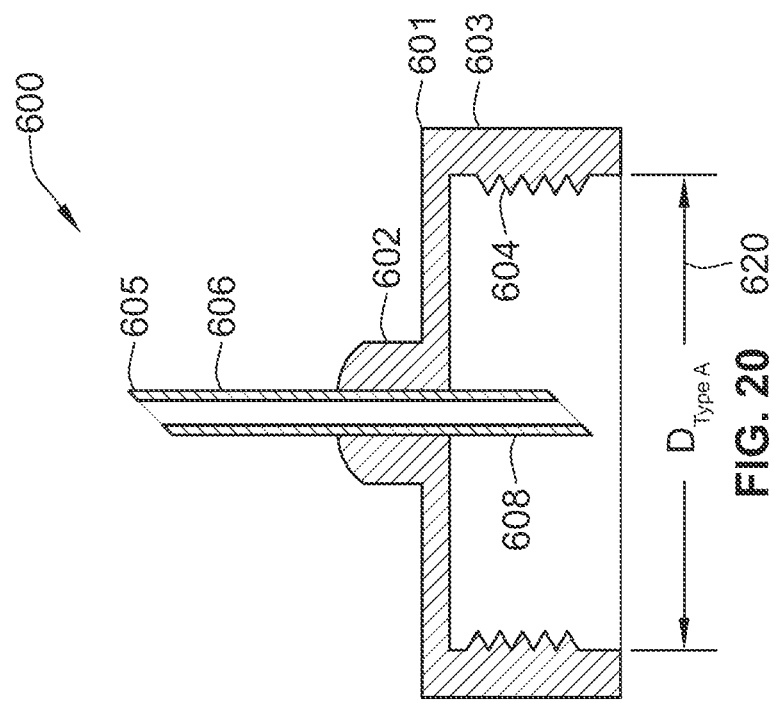
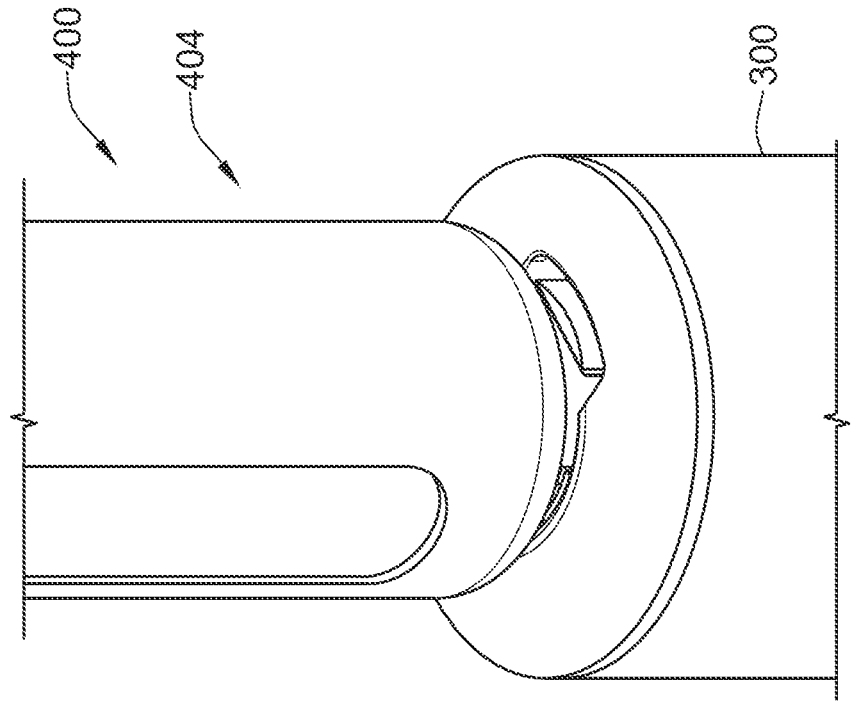

DEDICATED NEEDLE ASSEMBLY

CROSS REFERENCE TO RELATED APPLICATIONS

The present application is a 35 U.S.C. 371 National Application of PCT/EP2011/054418 filed Mar. 23, 2011 and claims priority to U.S. Patent Application No. 61/317,856, filed Mar. 26, 2010 and European Patent Application No. 10170208.1, filed Jul. 21, 2010, the entire contents of which are incorporated entirely herein by reference.

FIELD OF THE PRESENT DISCLOSURE

Specific embodiments of this disclosure relate to medical devices and methods of delivering at least two drug agents from separate reservoirs using devices having only a single dose setting mechanism and a single dispense interface. A single delivery procedure initiated by the user may cause a non-user settable dose of a second drug agent and a variable set dose of a first drug agent to be delivered to the patient. The drug agents may be available in two or more reservoirs, containers, or packages, each containing independent (single drug compound) or pre-mixed (co-formulated multiple drug compounds) drug agents. One aspect of the present disclosure is of particular benefit where the therapeutic response can be optimized for a specific target patient group, through control and definition of the therapeutic profile.

In another aspect of the present disclosure, a medicated module may comprise a dedicated needle assembly. With such a dedicated needle assembly, the needle assembly may only be used to administer a dose of a medicament that is contained within an associated dedicated drug delivery device, such as a dedicated pen-type drug delivery device. Alternatively, the needle assembly may comprise a non-medicated module, wherein the needle assembly may only be used with a dedicated drug delivery device. In one preferred embodiment, the dedicated needle assembly comprises a double ended needle.

BACKGROUND

There are a number of potential problems that can arise when delivering two active medicaments or "agents" simultaneously. The two active agents may interact with each other during the long-term, shelf life storage of the formulation. Therefore, there are certain advantages to storing the active components separately and then combining them at the point of delivery, e.g. injection, need-less injection, pumps, or inhalation. However, the process for combining the two agents needs to be straightforward and convenient for the user to perform reliably, repeatedly and safely.

A further potential concern is that the quantities and/or proportions of each active agent making up the combination therapy may need to be varied for each user or at different stages of their therapy. For example, one or more active agents may require a titration period to gradually introduce a patient to a "maintenance" dose. A further example would be if one active agent requires a non-adjustable fixed dose while the other is varied in response to a patient's symptoms or physical condition. This potential problem means that pre-mixed formulations of multiple active agents may not be suitable as these pre-mixed formulations would have a fixed ratio of the active components, which could not be varied by the healthcare professional or user.

Additional concerns may arise where a multi-drug compound therapy is required, because certain users cannot cope with having to use more than one drug delivery system or making the necessary accurate calculation of the required dose combination. This is especially true for users with dexterity or computational difficulties.

Other potential problems can arise where a user attempts to re-use a non-sterile needle assembly after a certain dose combination has been delivered. Using such non-sterile needle assemblies could lead to the transmission of certain diseases (septicemia) and, therefore, there exists a need for a medicated module that prevents needle re-use. There is a further concern of inadvertent needle sticks with certain needle assemblies where the injection needle is not concealed or covered, especially after use when a needle may be contaminated with blood. As such, there is also a general need to reduce certain patient's needle anxiety that may heighten a patient's fear or phobia of exposed needles. The medicated modules of the present disclosure may help to reduce this anxiety.

As described herein, in one situation, a patient would attach a medicated module to the drug delivery device in order to deliver the required combination dose of medication comprising a selected dose of the first medicament and a fixed dose of the second medicament. Following the administration of this combined dose, the single dose of medication within the medicated module would have been used and so features on the medicated module (such as a locking needle guard and/or visual warnings) would help to prevent the patient from being able to inject a second (non-combination) dose through the medicated module. A patient or user of the device would therefore be required to remove the used or spent medicated module and to attach a new medicated module to the drug delivery device for each dose administration.

An increasing number of drug delivery devices, such as pen-type drug delivery devices, are being marketed, including ones that are used for the delivery of different types of drugs. The issue of evident device and/or drug differentiation is becoming of increased importance as certain safety issues (some life-threatening) may arise which are associated with a patient or user mistaking one drug delivery device for another device and then administering an incorrect or wrong drug. While device/drug differentiation can be achieved in a number of ways, a preferable method of differentiation is mechanical prevention (i.e. making it difficult or nearly impossible for a device/drug mix up to occur). As just one example, a number of commercially available pen-type drug delivery devices are supplied with a coupling mechanism that is non-proprietary. That is, the coupling mechanism accommodates the attachment of a conventional Type A needle assembly according to EN ISO 11608-2:200 via a helical thread. Such a type A needle assembly may comprise an outer diameter of about 9.5 mm and an inner diameter of about 8.9 mm. The pitch may arise to 0.8. For the 'mono-product' devices, the use of different Type A needle assemblies is acceptable, as the needle assembly in this instance is simply the means of administering the medicament from the primary reservoir of the drug delivery device.

This may not be the case for the presently disclosed medicated module and systems, where inadvertent use of a medicated module with a non-approved primary drug delivery device could have serious consequences. Such consequences could include unknown health risks as the two formulations may not have been subject to any clinical evaluation or perhaps lacks regulatory approval. Equally, the use of a standard Type A needle with the approved primary drug delivery device may not be desirable, as a patient would not receive the targeted combination dose. In one situation, this might result in reduced therapeutic efficacy. However, in a worse situation, use of a standard Type A needle with the approved primary drug delivery device could result in non-desirable side effects, e.g. in the instance where the secondary medicament had some kind of balancing, cancelling or delaying effect on the pharmaco-kinetics ("PK") and/or pharmaco-dynamics ("PD") of the primary medicament contained within the drug delivery device. There are, therefore, certain safety and clinical benefits to configuring a combination delivery device which may prevent attachment of the medicated module to an incorrect primary drug delivery device. There are also, therefore, certain benefit, e.g. regarding safety and clinical benefits, to configure a combination delivery device so as to prevent attachment of a standard or conventional Type A needle to the combination therapy's primary drug delivery device.

Accordingly, there exists a need to provide devices and methods for the delivery of two or more medicaments in a single injection or delivery step that is simple and safe for the user to perform and that also tends to reduce a patient's anxiety towards injections or needles or combinations of drug therapies. The presently disclosed dedicated needle assemblies and administration systems overcome the above-mentioned concerns by providing separate storage containers for two or more active drug agents that are then combined and/or administered during a single delivery procedure. Such devices may be provided in separate storage containers or provided in a kit form comprising at least one medicated module and at least one non-medicated module with dedicated attachments between each other.

Setting a dose of one medicament may automatically fix or determine the dose of the second medicament (i.e. a non-user settable medicament). The present disclosure may also give the opportunity for varying the quantity of one or both medicaments. For example, one fluid quantity can be varied by changing the properties of the injection device, e.g. by dialling a user variable dose or changing the device's "fixed" dose. The second fluid quantity can be changed by manufacturing a variety of secondary drug containing packages or kits with each variant containing a different volume and/or concentration of the second active agent. The user or healthcare professional would then select or prescribe the most appropriate secondary package or series or combination of series of different packages or kits for a particular treatment regime. These and other advantages will become evident from the following more detailed description of the invention.

Problem to be Solved

The problem to be solved by the present invention is to provide a needle assembly and a drug delivery system where the safety for the user is improved.

SUMMARY

The present disclosure discloses modules, systems, methods, drug delivery devices and kits that may allow for the complex combination of multiple drug compounds within a single drug delivery system. Preferably, such a system includes a needle guard that may function to prevent needle assembly re-use and that can also function to reduce needle phobia while also reducing potential inadvertent needle sticks. Such a system may also include a containment of a (secondary) drug compound within a needle sub-assembly, what will be referenced as a medicated module in the context of this disclosure.

A user can set and dispense a multi-drug compound through one single dose setting mechanism and a single drug dispense interface. Preferably, the single drug dispense interface may then be locked out so as to prevent re-use of a medicated module (i.e. re-use of the injection needle). This single dose setter may control the mechanism of the device such that a predefined combination of the individual drug compounds is delivered when a single dose of one of the medicaments is set and dispensed through the single drug dispense interface.

By defining the therapeutic relationship between the individual drug compounds the presently disclosed delivery devices and systems would help ensure that a patient/user receives the optimum therapeutic combination dose from a multi-drug compound device without the inherent risks associated with multiple inputs where the user has to calculate and set the correct dose combination when they use the device. The medicaments can be fluids, defined herein as liquids or gases that are capable of flowing and that may change shape at a steady rate when acted upon by a force tending to change its shape. Alternatively, one of the medicaments may be a solid that is carried, solubilized or otherwise dispensed with another fluid medicament.

The present disclosure is of particular benefit to patients with dexterity or computational difficulties as the single input and associated predefined therapeutic profile may remove the need for them to calculate their prescribed dose when they use the device and the single input may allow considerably easier setting and dispensing of the combined compounds. This disclosure is also of particular benefit to patients experiencing needle phobia or who may experience a general fear of inadvertent needle sticks.

In a preferred embodiment a master or primary drug compound, such as insulin, contained within a multiple dose, user selectable drug delivery device could be used with a single use, user replaceable, medicated module that contains a single dose of a secondary medicament and the single dispense interface. When connected to the primary device, the secondary compound is activated/delivered on dispense of the primary compound. Although the present disclosure specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of the present disclosure, the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg (B32) human insulin; Lys(B3), Glu(B29) human insulin; Lys(B28), Pro(B29) human insulin; Asp(B28) human insulin: human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N- palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly- Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys- Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

One aspect of the present disclosure relates to a needle assembly. The needle assembly may be a dedicated needle assembly. The needle assembly may be a double ended needle assembly, for example. The needle assembly may be configured to be, preferably releasably, attached to a dedicated drug delivery device. The needle assembly may comprise a dedicated mechanical coupling. Said dedicated mechanical coupling may be adapted and arranged to form a, preferably releasable, connection to a distal end section, in particular a distal end of the dedicated drug delivery device. Such dedicated mechanical coupling may be configured such that the primary drug delivery device and the medicated module are exclusively matched by non-standard designs, i.e. non Type A-designs. For example a dedicated needle assembly may be configured by means of a dedicated mechanical coupling to be attached to a dedicated drug delivery device. The dedicated mechanical coupling however, may be adapted and arranged to form a connection to a distal end section of the dedicated drug delivery device.

The dedicated needle assembly may be attachable only to the dedicated drug delivery device. A dedicated drug delivery device may, for example, be a device comprising a mechanical coupling, e.g. provided on a distal end of a cartridge holder of the dedicated device, which coupling is different from a screw thread. Alternatively, the dedicated drug delivery device may be a device comprising a coupling member, e.g. an adapter, comprising the dedicated mechanical coupling at its distal end, e.g. a coupling which is different from a screw thread. Said coupling member may comprise the cartridge holder or a cap mountable on the cartridge holder of the device, which is explained later on in more detail. The dedicated needle assembly may comprise a connecting body. The connecting body may extend from a distal end to a proximal end of the needle assembly. The dedicated mechanical coupling may be configured at the proximal end section, in particular at the proximal end, of the connecting body. This dedicated mechanical coupling may be configured to form a, preferably releasable, connection to a distal end section of the dedicated drug delivery device. The dedicated mechanical coupling of the dedicated needle assembly may be configured to prevent a connection of the dedicated needle assembly to a drug delivery device, where the drug delivery device comprises a conventional mechanical coupling, such as a conventional screw type thread. The dedicated mechanical coupling may be integral to the needle assembly.

According to an embodiment, said needle assembly is configured to define an engaging cavity. The engaging cavity may be adapted and arranged to mechanically cooperate with the dedicated drug delivery device to form the, preferably releasable, connection. Said engaging cavity may comprise an engaging cavity diameter. The engaging cavity may comprise a first engaging cavity diameter. The engaging cavity may comprise a second engaging cavity diameter. The respective engaging cavity diameter may be provided on that end of the needle assembly which is configured to be connected to the distal end section of the device, e.g. the proximal end of the needle assembly. The engaging cavity diameter, in particular the first engaging cavity diameter, may be configured to define a width that is less than a diameter of a conventional needle assembly, e.g. a needle assembly comprising a screw thread as mechanical coupling.

According to an embodiment, the engaging cavity comprises an inner wall. Said dedicated mechanical coupling may comprise a plurality of protrusions. The protrusions may be located along this inner wall. Said plurality of protrusions may be configured to mechanically cooperate with, in particular to be, preferably releasably, coupled to, at least one groove. The at least one groove may be positioned in the distal end section of the dedicated drug delivery device.

According to an embodiment, said dedicated mechanical coupling further comprises a plurality of recesses. The recesses may be defined along this inner wall. Said plurality of recesses may be configured to mechanically cooperate with, in particular to be, preferably releasably, coupled with, at least one bump feature. The at least one bump feature may be positioned in the distal end section of the dedicated drug delivery device.

According to an embodiment, said needle assembly comprises a medicated module. Alternatively, said needle assembly may comprise a non-medicated module, e.g. a module that does not comprise a secondary drug compound.

According to an embodiment, the needle assembly, in particular the medicated module, further comprises a connecting body. The connecting body may extend from a distal end to a proximal end of the medicated module. Said medicated module may further comprise a first needle. Said medicated module may further comprise a second needle. Said medicated module may further comprise an outer body. The outer body may be operatively coupled to said connecting body. Said medicated module may further comprise a needle guard. The needle guard may be operatively coupled to said outer body. The needle guard may be adapted and arranged to provide protection of the needle. Said medicated module may further comprise a biasing element. The biasing element may be positioned between said outer body and said needle guard. The biasing element may be configured to exert a force, preferably an axially directed force, onto the needle guard. The medicated module may further comprise a recess. The recess may be arranged within said connecting body. The recess may define a reservoir. Said reservoir may contain at least one dose of a medicament. Said reservoir may be configured for fluid communication with said needle.

According to an embodiment, the needle assembly, in particular the non-medicated module, comprises a double ended needle. The non-medicated module may comprise a needle guard. The needle guard may be adapted and arranged to provide protection of the double ended needle. When said needle assembly is mounted onto said dedicated drug delivery device, said double ended needle may be adapted and arranged to reside in fluid communication with a medicament contained within said drug delivery device.

A further aspect relates to a dedicated coupling member for a drug delivery device. Said coupling member may comprise a dedicated mechanical coupling. Said dedicated mechanical coupling may be configured to form a, preferably removable, connection to the dedicated needle assembly described above.

According to an embodiment, the coupling member is configured to be arranged in the end section of the device which is configured to be connected to the dedicated needle assembly, e.g. the distal end section of the device. The coupling member may be part of a, preferably dedicated, drug delivery device. The drug delivery device may for example be configured to be connected to the dedicated needle assembly. Alternatively, the coupling member may be configured to be connected to a, preferably conventional, drug delivery device, e.g. a device comprising a conventional screw thread.

The coupling member may comprise a dedicated cartridge holder, for example. The cartridge holder may be part of a dedicated drug delivery device. The cartridge holder may be adapted and arranged to be connected, preferably releasably connected, to the distal end section of the device. The cartridge holder may comprise a tubular member. The tubular member may extend from a proximal end of said cartridge holder to a distal end of said cartridge holder. The cartridge holder may comprise a generally cylindrical extension. The cylindrical extension may extend from a proximal end near a shoulder of said cartridge holder. The dedicated coupling mechanism may be provided on said generally cylindrical extension. The dedicated mechanical coupling may be configured to form a, preferably releasable, connection to the engaging cavity of the dedicated needle assembly.

In one alternative arrangement, the dedicated mechanical coupling of the cartridge holder is configured to prevent a connection of the dedicated cartridge holder to a, preferably double ended, needle assembly, where the double ended needle assembly comprises a conventional screw type coupling. In one arrangement, the dedicated mechanical coupling may be integral to the dedicated cartridge holder.

Alternatively, the coupling member may comprise a dedicated cap. The cap may be adapted and arranged for use with a conventional drug delivery device. The cap may comprise an adapter or an interface configured to adapt the conventional drug delivery device to a dedicated needle assembly, for example. In particular, the cap may be configured to act as a connector, i.e. to enable connection, of the dedicated needle assembly and the conventional drug delivery device. The cap may be configured to establish a, preferably releasable, connection between the conventional drug delivery device and the dedicated needle assembly. The cap may comprise a main body. The cap may comprise a generally cylindrical extension. The extension may extend from said main body. The cap may comprise the dedicated coupling mechanism described above. The dedicated coupling mechanism may be provided on said generally cylindrical extension.

According to an embodiment, said dedicated mechanical coupling comprises at least one, preferably a plurality of grooves. The grooves may be arranged in a distal portion of the coupling member. Said plurality of grooves may be configured to mechanically cooperate with, in particular to couple with, at least one protrusion positioned within the engaging cavity of the previously described dedicated needle assembly.

According to an embodiment, the coupling member comprises a screw thread. The screw thread may be provided on an inner surface, e.g. an inner surface of a main body, of said coupling member. Said screw thread may be configured to be, preferably releasably, threadedly coupled to a drug delivery device having a conventional screw thread coupling.

According to an embodiment, the dedicated coupling provided may be configured to form said, preferably releasable, connection to said engaging cavity of said dedicated needle assembly, wherein said dedicated needle assembly comprises a medicated module or a non-medicated module.

A further aspect relates to a drug delivery kit for a drug delivery device. Said kit may comprise a first dedicated needle assembly. The first dedicated needle assembly may be configured for, preferably releasable, connection to a drug delivery device. Said first dedicated needle assembly may comprise a medicated module. Said kit may comprise a second dedicated needle assembly. The second dedicated needle assembly may be configured for, preferably releasable, connection to said drug delivery device. Said second dedicated needle assembly may comprise a non-medicated module.

According to an embodiment, said drug delivery kit comprises a plurality of first dedicated needle assemblies. The dedicated needle assemblies may be configured for, preferably releasable, connection to said drug delivery device.

A particular benefit of this disclosure is that the medicated module makes it possible to tailor dose regimes when required, especially where a titration period is necessary for a particular drug. The medicated module could be supplied in a number of titration levels with differentiation features such as, but not limited to, aesthetic design of features or graphics, numbering etc., so that a patient could be instructed to use the supplied medicated module in a specific order so as to facilitate titration. Alternatively, the prescribing physician may provide the patient with a number of "level one" titration medicated modules or a kit of modules and then, when these were finished, the physician could then prescribe the next level or the next drug delivery kit. One advantage of this titration program is that the primary device can remain constant throughout.

A mechanical dedication of both the drug delivery device and the medicated module provides a solution that may allow attachment only of a specific medicated module to a specific primary device. The use of the primary device with a standard (Type A) needle may not be desirable, as a patient would not receive the combination dose as prescribed, e.g.

Another particular benefit of the proposed dedicated needle assemblies and assembly systems is that they provide a mechanical device-based solution that can be used to achieve certain advantages. Such advantages include facilitating attachment of the dedicated needle assembly (e.g. a medicated module) to a correct primary drug delivery device by a patient or user. The presently disclosed dedicated needle assemblies may also help to prevent accidental or inadvertent attachment of the dedicated needle assembly to a non-approved drug delivery device that comprises a conventional needle assembly fitting, such as a standard or conventional Type A fitting. In addition, dedicated needle attachment features may also prevent a patient or user from accidentally attaching a standard Type A needle to the combination therapy's primary drug delivery device.

In order to facilitate split dosing scenarios (e.g. end of cartridge scenario, split for volume, etc.), specific non-medicated modules or "zero-dose" needle assemblies could be supplied and/or made available to patients for use with the combination delivery system which utilize the same or similar dedicated mechanical attachment features. The term non-medicated module is used for a needle sub-assembly that does not comprise a containment of a (secondary) drug compound. Supply of such non-medicated needle assemblies might either be in a controlled manner, e.g. supply of a single 'zero-dose' needle alongside each replacement primary drug delivery device (to accommodate end of cartridge dose splitting, if required), or in a managed manner, e.g. via prescription (e.g. for patients whose regular dose of the medication in the primary drug delivery device is greater than the maximum dose the device can deliver in a single injection and who, therefore, are forced to split their dose into two or more separate injections), or in a direct access manner (e.g. over the counter from a Pharmacy). In addition, where 'zero-dose' needles are dedicated and also single use, this tends to help control the ability to use them indiscriminately.

Additionally, if the dedicated needle assemblies were to be used for scenarios where multiple secondary medicaments could be used (e.g. a long-acting insulin along with a first drug type "Drug A", a long-acting insulin along with a second drug type "Drug B", a long-acting insulin along with a third drug type 'Drug C'), or where multiple (but independently exclusive) combination therapies were to be marketed ('Drug A' plus 'Drug X', 'Drug B' plus 'Drug Y', 'Drug C' plus 'Drug Z', etc.) then it might be desirable for the exclusive or proprietary dedicated mechanical coupling to also include specific coding features and/or mechanical attributes to maintain exclusivity while also allowing a level of controlled differentiation within a family of combination therapies. One advantage of such a situation is that this would potentially enable the same basic dedicated mechanical coupling of the dedicated needle assemblies to be used (e.g. push to fit, pull to detach) across all supplied drug delivery devices or all devices contained within a family of drug delivery devices. This would, thereby, help preserve the usability benefits of the selected approach, while also providing a means for mechanical differentiation and/or dedication to help reduce the risk of patient mix-up between individual drugs from the family of combination therapies that used the system.

In a preferred embodiment, the primary drug delivery device is used more than once and, therefore, is multi-use. Such a device may or may not have a replaceable reservoir of the primary drug compound, but the needle assembly and the coupling member described above may be equally applicable to both scenarios. It is possible to have a suite of different medicated modules for various conditions that could be prescribed as one-off extra medication to patients already using a standard drug delivery device (or family of devices). Should the patient attempt to re-use a previously used medicated module, the presently disclosed medicated module can provide a lockable needle guard feature that could alert the patient to this situation. Other means of alerting the user may include some (or all) of the following:

Physical prevention of medicated module re-attachment to the primary drug delivery device once the module was used and removed.

Physical prevention of insertion of the used drug dispense interface into the patient (e.g. a single use needle-guard type arrangement).

Physical/hydraulic prevention of subsequent liquid flow through the drug dispense interface once it has been used.

Physical locking of the dose setter and/or dose button of the primary drug delivery device.

Visual warnings (e.g. change in color and/or warning text/indicia within an indication window on the module once needle insertion and/or fluid flow has occurred).

Tactile feedback (presence or absence of tactile features on the outer surface of the module hub following use).

According to a preferred embodiment, a dedicated needle assembly is provided which is configured to be attached to a dedicated drug delivery device, said dedicated needle assembly comprising a dedicated mechanical coupling. Said dedicated mechanical coupling is adapted and arranged to form a connection to a distal end section of the dedicated drug delivery device.

According to a preferred embodiment, a dedicated needle assembly is provided that can only be attached to a dedicated drug delivery device, said dedicated needle assembly comprising a connecting body extending from a distal end to a proximal end and a dedicated mechanical coupling configured at said proximal end of said connecting body. Said dedicated mechanical coupling forms a releasable connection to a distal end of a dedicated drug delivery device.

According to a preferred embodiment, a dedicated coupling member for a drug delivery device is provided, said coupling member comprising a dedicated mechanical coupling. Said dedicated mechanical coupling is configured to form a connection to the previously described dedicated needle assembly.

According to a preferred embodiment, a dedicated cartridge holder is provided, said cartridge holder comprising a tubular member extending from a proximal end of said cartridge holder to a distal end of said cartridge holder, a generally cylindrical extension extending from a proximal end near a shoulder of said cartridge holder and a dedicated coupling mechanism provided on said generally cylindrical extension. Said dedicated mechanical coupling is configured to form a releasable connection to an engaging cavity of a dedicated needle assembly.

According to a preferred embodiment, a dedicated cap for use with a conventional drug delivery device is provided, said cap comprising a main body,
a generally cylindrical extension extending from said main body, a dedicated coupling mechanism provided on said generally cylindrical extension, and
a screw thread provided on an inner surface of said main body. Said dedicated mechanical coupling is configured to form a releasable connection to an engaging cavity of a dedicated needle assembly.

According to a preferred embodiment, a drug delivery kit for a drug delivery device is provided, said kit comprising a first dedicated needle assembly configured for connection to a drug delivery device, said first dedicated needle assembly comprising a medicated module, and a second dedicated needle assembly configured for connection to said drug delivery device, said second dedicated needle assembly comprising a non-medicated module.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which:

FIG. 12 illustrates a perspective view of the dedicated drug delivery device illustrated in FIG. 11 just prior to being inserted into the dedicated needle assembly illustrated in FIG. 10 where the dedicated drug delivery device is not aligned with the dedicated needle assembly;

FIG. 13 illustrates a perspective view of the dedicated drug delivery device partially inserted into the dedicated needle assembly illustrated in FIG. 10 where the dedicated drug delivery device is still not aligned with the dedicated needle assembly;

FIG. 16 illustrates a perspective view of the distal end of the dedicated drug delivery device after the device has been fully inserted into the dedicated needle assembly illustrated in FIG. 10;

FIG. 20 illustrates a perspective view of a standard needle arrangement that can be used with a drug delivery device having a conventional threaded distal end, such as the device illustrated in FIG. 9.

DETAILED DESCRIPTION

In the present disclosure, a fixed predetermined dose of a second medicament (secondary drug compound) and a potentially variable dose of a first medicament (primary drug compound) are administered through a single output or drug dispense interface such as a double ended needle. Setting the dose of the primary medicament by the user may automatically determine the fixed dose of the second medicament. This fixed dose of the second medicament is preferably a single dose. In a preferred arrangement, the drug dispense interface comprises a needle cannula (hollow needle) and a needle guard that may be locked out after medicament injection.

Figure 1:
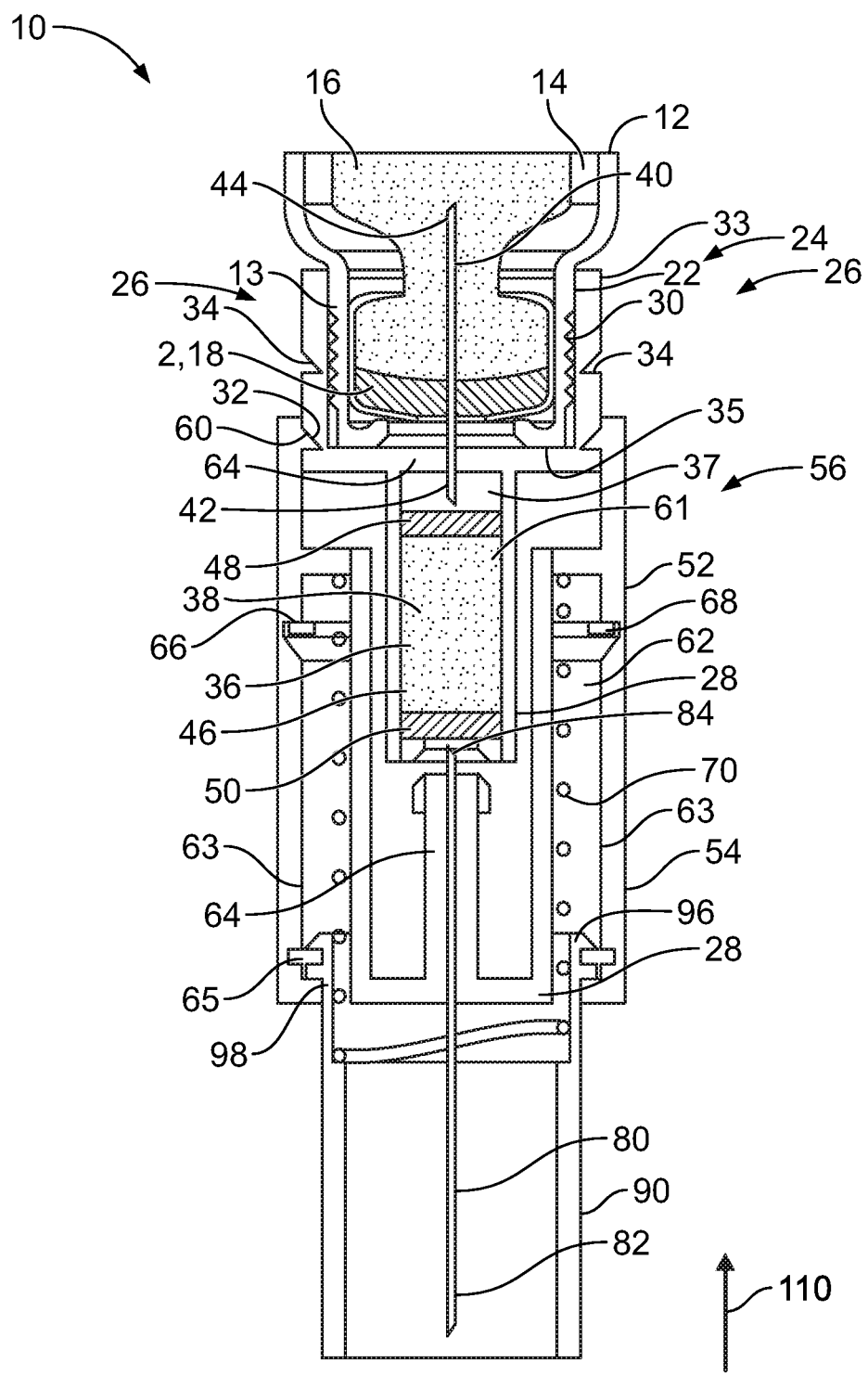
FIG. 1 illustrates a sectional view of one needle assembly arrangement comprising a medicated module that is attached to a drug delivery device having a conventional screw thread.

FIG. 1 illustrates a sectional view of one needle assembly arrangement comprising a medicated module 10 that is attached to a drug delivery device 12 having a conventional screw thread 30. As illustrated, the medicated module 10 comprises a first needle 40 that pierces a septum 2 of a device cartridge 14. A second injection needle 80 is used to subcutaneously inject the first medicament contained in the cartridge 14 along with a second medicament contained in the medicated module 10. Located between the two needles 40, 80 is a recess 37 defined by a connection body 24. Preferably, this recess 37 contains a reservoir of the second medicament 38. Most preferably, this reservoir 37 comprises a capsule 46 that has ends sealed with first and a second pierceable seals 48, 50, respectively.

In this preferred arrangement, the medicated module 10 as illustrated is attached to the drug delivery device 12. Only a portion of such a drug delivery device 12 is illustrated in FIG. 1. The drug delivery device 12 comprises a cartridge holder containing the standard cartridge 14. This standard cartridge 14 comprises a first medicament 16 such as insulin or the like.

In one arrangement, the medicated module 10 is preferably self-contained and may be provided as a sealed and sterile disposable module. Such a module comprises an attachment means compatible to the attachment means at a distal end of the drug delivery device 12. As described in greater detail below, the medicated module 10 could be supplied by a manufacturer contained in a protective and sterile container where the user would peel or rip open a seal or the container itself to gain access to the sterile medicated module. In some instances it might be desirable to provide two or more seals for each end of the medicated module 10. In addition, and as will be explained in greater detail below, in one arrangement, such medicated module 10 may be provided in a drug delivery kit along with at least one non-medicated module, such as the non-medicated module illustrated in FIG. 5.

Figure 9:
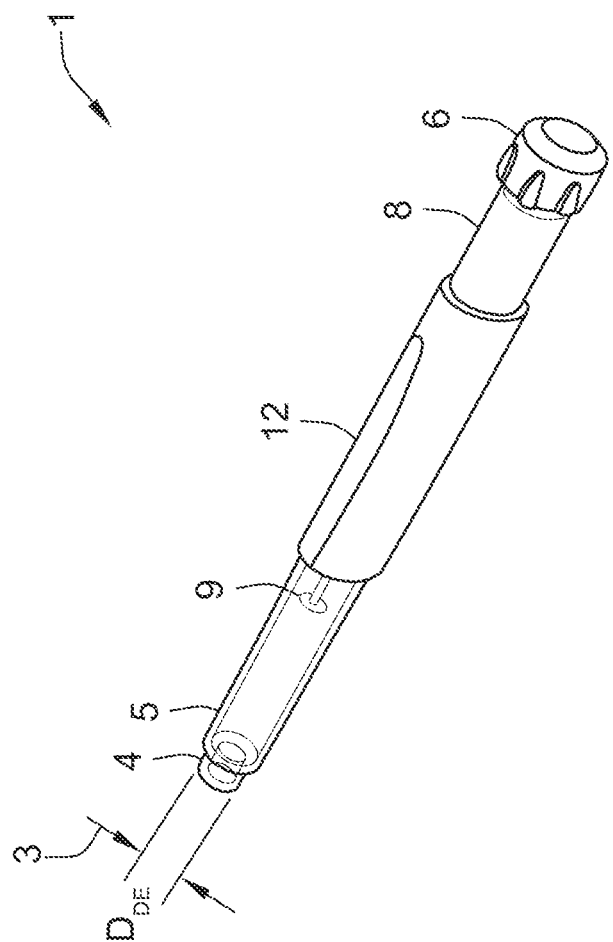
FIG. 9 illustrates one possible drug delivery device that can be used with the medicated module illustrated in FIG. 1.

One example of a drug delivery device 1 is illustrated in FIG. 9. Referring to FIG. 9, there is shown a conventional drug delivery device 1 in the form of a pen-type drug delivery device. This drug delivery device 1 comprises a dose setting mechanism 6, a cartridge holder 5, and a removable cap. The cartridge holder 5 comprises a tubular member 7 that extends from a proximal end to a distal end. The distal end of the cartridge holder 5 comprises a coupling mechanism 4 for releasably coupling a dispense interface, such as a double ended needle assembly. In this conventional drug delivery device 1, this distal end 4 defines a distal end diameter DDE 3 and this coupling mechanism 4 comprises a conventional screw thread.

The proximal end of the cartridge holder 5 and the distal end of the dose setting mechanism 6 are secured together. The pen-type drug delivery device 1 may comprise a re-usable or a disposable pen-type drug delivery device. Where the drug delivery device 1 comprises a re-usable device, the cartridge holder 5 and the dose setting mechanism 6 are removably coupled together. In a disposable device, they are permanently coupled together. The dose setting mechanism 6 comprises an outer housing that extends from a proximal end to a distal end of the dose setting mechanism 6. In one preferred arrangement, the housing contains a piston rod 9, such as a threaded piston rod that rotates when a dose is injected.

To inject a previously set dose, a conventional double ended needle assembly is attached to the conventional thread screw 4 provided at the distal end of the tubular member of the cartridge holder 5. FIG. 20 illustrates such a conventional needle assembly 600.

FIG. 20 illustrates a cross sectional view of a conventional double ended needle assembly 600. The needle assembly 600 illustrated in FIG. 20 comprises a double ended needle 606 and a hub 601. The double ended needle or cannula 606 is, preferably, fixedly mounted in a needle hub 601. This needle hub 601 comprises a circular disk shaped element which has along its periphery a circumferential depending sleeve 603. Along an inner wall of this hub member 601, a conventional thread 604 is provided. This thread 604 allows the needle hub 601 to be screwed onto the distal end of the drug delivery device which is provided with a corresponding outer thread along a distal hub. At a center portion of the hub element 601 there is provided a protrusion 602. This protrusion 602 projects from the hub 601 in an opposite direction of the sleeve member. A double ended needle 606 is mounted centrally through the protrusion 602 and the needle hub 601. This double ended needle 606 is mounted such that a first or distal piercing end 605 of the double ended needle forms an injecting part for piercing an injection site (e.g., the skin of a user).

Similarly, a second or proximal piercing end 608 of the needle assembly 600 protrudes from an opposite side of the circular disc so that it is concentrically surrounded by the sleeve 603. In one needle assembly arrangement, the second or proximal piercing end 608 may be shorter than the sleeve 603 so that this sleeve to some extent protects the pointed end of the double ended needle 606.

Returning to FIG. 1, the illustrated arrangement has the benefit of the second medicament 38 as a single dose being contained entirely within the medicated module 10. This can minimize the risk of material incompatibility between the second medicament 38 and the materials used in the construction of the medicated module 10. The medicated module 10 comprises a connecting body 24, a first needle 40, an outer body 52, a second needle 80, a biasing member 70, and a needle guard 90.

The connecting body 24 extends from a proximal end 26 to a distal end 28 The proximal end of the connecting body 24 is provided with a connector 30 so that the medicated module 10 may be connected to the drug delivery device 12. Preferably, this connector 30 is provided along an inner surface 22 of the connecting body 24 and provides a releasable connection to the drug delivery device 12. Such a releasable connector 30 may comprise a snap fit, form fit, snap lock, luer lock or other similar connection mechanism known to those of skill in the art. As can also be seen from FIG. 1, the connecting body 24 further comprises a first and second recess 32, 34. These recesses 32, 34 are provided along a connector body external surface 33. Although only two recesses 32, 34 are illustrated in the medicated module 10 arrangement illustrated in FIG. 1, alternative recess arrangements may comprise more or less than two recesses 32, 34. As will be explained in greater detail below, as illustrated in FIG. 1, a male member 60 of an outer body 52 is releasably engaged to the first recess 32.

The connecting body 24 defines a reservoir 36 and preferably this reservoir 36 contains the second medicament 38. Most preferably, this second medicament 38 comprises a single dose of a medicament, such as a single dose of GLP-1 or alternatively a pre-mix of medicaments. In one preferred arrangement, the reservoir 36 comprises a capsule 46 comprising a first and a second end that is sealed with pierceable membranes 48, 50. Such a construction provides a hermetically sealed reservoir for the second medicament 38.

The connecting body 24 further comprises a first needle 40 rigidly affixed in an upper surface 35 of the connecting body. 24 Preferably, this first needle 40 comprises a double ended needle having a first piercing end 42 (e.g. a distal end) and a second piercing end 44 (e.g. a proximal end). In this preferred arrangement, when the medicated module 10 is initially mounted to the drug delivery device 12 as illustrated in FIG. 1, the first piercing end 42 pierces the membrane 18 of the cartridge 14 but the second piercing end 44 does not yet pierce the first or proximal seal 48 of the capsule 46. As such, the first medicament 16 of the cartridge 14 is not in fluid communication with the second medicament 38 contained in the capsule 46.

Figure 2:
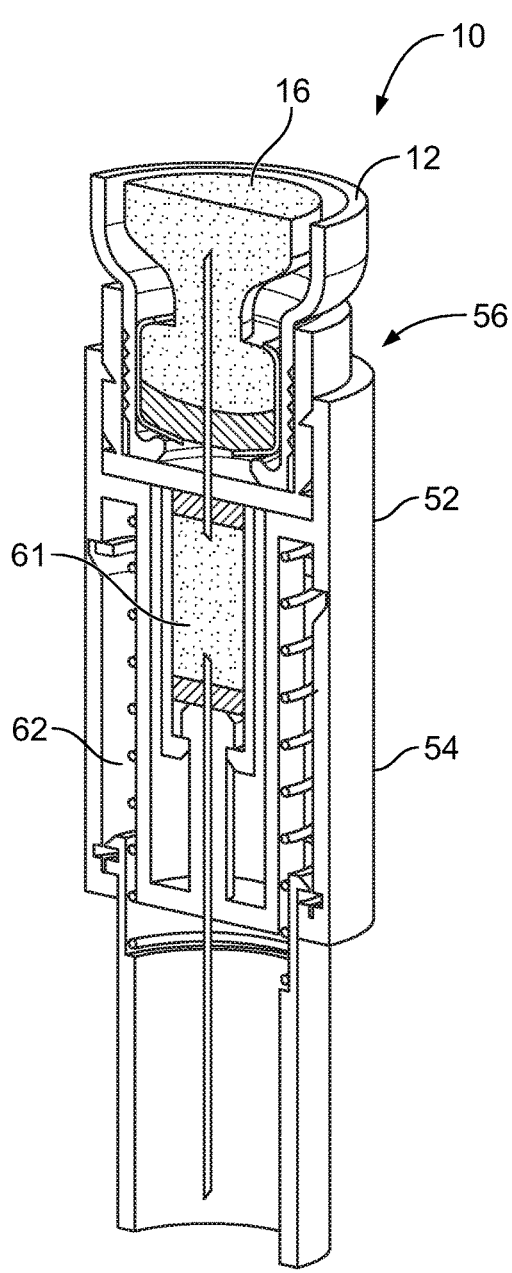
FIG. 2 illustrates a perspective view of the medicated module of FIG. 1 having two needles connected to a reservoir attached to a drug delivery device.
Figure 3:
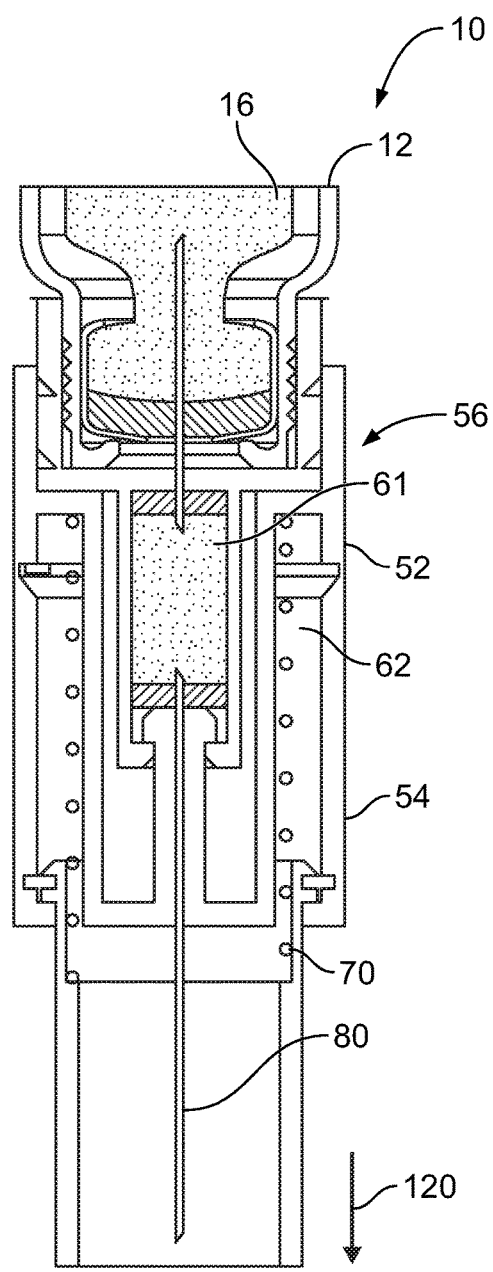
FIG. 3 illustrates a front view of the medicated module of FIG. 2.
Figure 4:
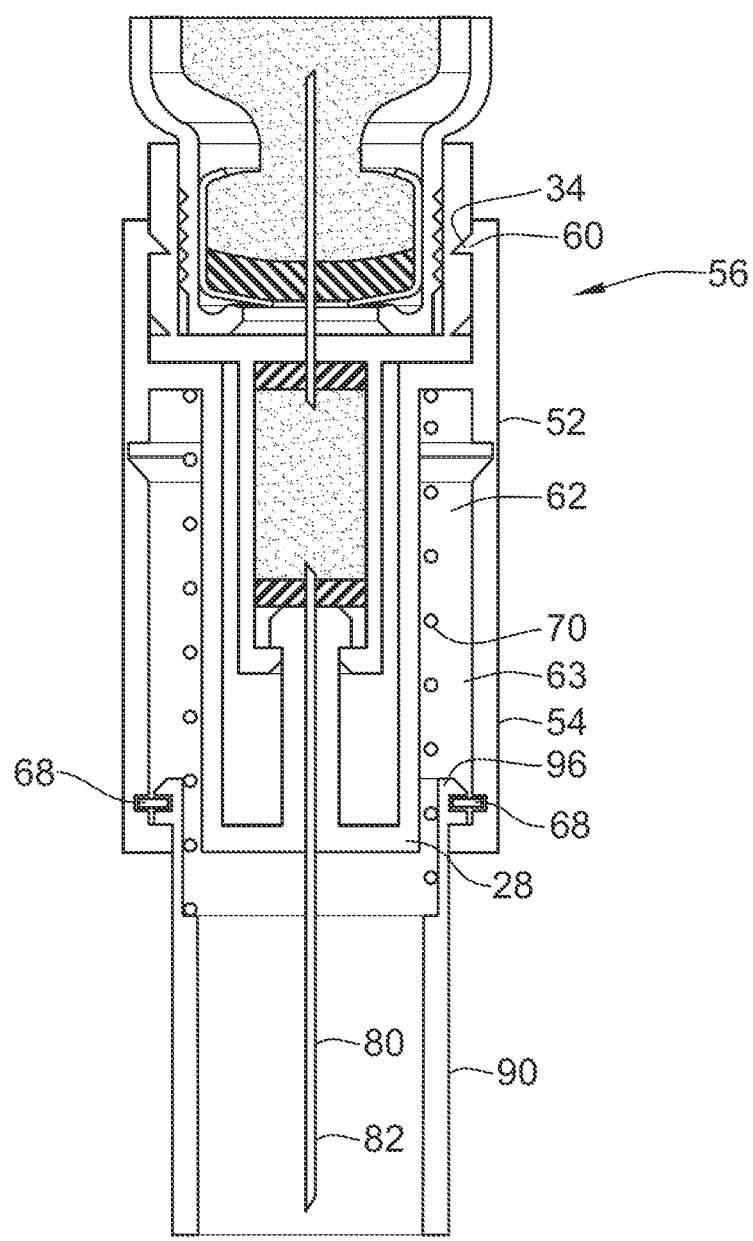
FIG. 4 illustrates the medicated module illustrated in FIG. 1 having a locked out needle guard.

The medicated module 10 further comprises an outer body 52 and preferably this outer body 52 is slidably engaged with the connecting body 24. More preferably, this outer body 52 is slidably engaged with the connecting body 24 and is slidable from an initial position (as illustrated in FIG. 1) to a second or dose injecting position (as illustrated in FIGS. 2 and 3).

The outer body 52 comprises a distal end 54 and a proximal end 56. The outer body proximal end 56 is configured with a male member 60 that releasably engages the connecting body 24. Preferably, when the medicated module 10 is initially mounted onto the drug delivery device 12 as illustrated in FIG. 1, the male member 60, preferably, releasably engages the first recess 32 provided along the outer surface 33 of the connecting body 24. In the second or dose injecting position (as illustrated in FIGS. 2 and 3), the male member 60 is moved proximally so that this member 60 engages the second recess 34.

The outer body 52 further comprises a first and a second inner cavity 61, 62 respectively. Preferably, the first inner cavity 61 is formed to contain the reservoir 36 of the connecting body 24 whereas the second inner cavity 62 is formed to contain an elastic member 70, such as a compression spring. As illustrated in FIG. 1, in the initial mounted position of the medicated module 10, the elastic member 70 is in an extended state. In this extended state, the elastic member 70 resides within this second cavity 62 and between the outer body 52 and the needle guard 90.

The outer body 52 further comprises a distal and a proximal groove 65, 66 provided on inner surface 52. The proximal groove 65 includes a movable locking feature 68, preferably in the form of a movable circlip. As will be explained below, this movable locking feature 68 is used to lock out the needle guard 90 after injection that is, after the needle guard 90 is first moved in a proximal direction and then returned in a distal direction.

The outer body 60 further comprises a second or injection needle 80 rigidly affixed in outer body hub element 64. Preferably, this second needle 80 comprises a double ended needle having a first piercing end 82 (i.e., a distal end) and a second piercing end 84 (i.e., a proximal end).

In this preferred arrangement, when the medicated module 10 is initially mounted to the drug delivery device 12 as illustrated in FIG. 1, the second piercing end 84 does not yet pierce the distal seal 50 of the capsule 46. In addition, in this preferred arrangement, the first piercing end 82 of the second needle 80 is illustrated as being substantially concealed from a user's view by way of the needle guard 90 so as to help reduce any needle anxiety that a patient may be experiencing.

Preferably, needle guard 90 comprises a tubular shaped element and in a relaxed position, as illustrated in FIG. 1, substantially conceals the second needle 80. While substantially concealing the second needle 80, the needle guard 90 also helps to prevent inadvertent needle sticks. In FIG. 1, this needle guard 90 is illustrated in an unlocked position. That is, during an injection step where a user initiates the injection, the needle guard 90 may be free to be moved in a proximal direction or towards the drug delivery device 12 (illustrated by arrow 110 in FIG. 1).

Preferably, the needle guard 90 comprises a plurality of outwardly directed arms 96, 98. These arms 96, 98 are in sliding engagement with an inner surface 63 of the inner cavity 62 of the outer body 52 and reside within the second cavity 62 defined by the outer body 52. These outwardly directed arms 96, 98 allow for the needle guard 90 to be placed and held in a locked out position after dose injection. In addition, these outwardly directed arms 96, 98 may also serve to prevent a rotation, in particular to prevent the needle guard 90 from rotating either when it is connected to the drug delivery device 12 or during the medicament injection step.

As shown in FIG. 1, in this first position, the outer body 52 comprises at a proximal end inwardly extending male members 60 that engage the first recess 32 provided near the proximal end of the connecting body 24. When the outer body 52 resides in this initial connected or mounting position, the inwardly extending male members 60 engage the first set of recesses 32 of the connecting body and both the first and the second needles 40, 80 are not in fluid communication with the medicated module reservoir 36.

As discussed above, in the initial mounting position, both the first and the second needles 40, 80 are not in fluid communication with the medicated module reservoir 36. FIG. 3 illustrates a side view of attachment of the medicated module 10 to the drug delivery device 12 in a dose ready state. To achieve this dose ready state or second state, the outer body 52 is moved in the proximal direction. This outer body proximal movement causes the inwardly extending male members 60 of the outer body 52 to move from the first recess 32 to the second recess 34 of the connecting body 24.

Importantly, proximal movement of the outer body 52 may also cause the distal end 42 of the first needle 40 to penetrate the first pierceable seal 48 of the capsule 46 while the proximal end 44 of first needle 40 maintains its penetration of the septum of the cartridge 14 of the device 12. Proximal movement of the outer body 52 may also cause the proximal end 84 of the second needle 80 to penetrate the second pierceable seal 50 of the capsule 46. Piercing of membranes 48 and 50 opens fluid communication between the first and second medicaments 16, 38 allowing these two medicaments 16, 38 to be dispensed through operation of the dispense mechanism on the drug delivery device 12.

Where the drug delivery device 12 comprises a dose setter 8, a dose of the drug delivery device 1 may then be set using said dose setter 8 (see FIG. 9) in the normal manner (e.g., by dialing out the appropriate number of units). Dispense of the medicaments 16, 38 may then be achieved by subcutaneously injecting the medicaments 16, 38 via activation of a dose button on device 12. The dose button 6 may be any triggering mechanism that causes the dose of the first medicament 16 that was set by the dose setter 8 to move distally towards the distal end of the device 12. In a preferred embodiment, the dose button 12 is operably connected to a spindle that engages a piston in the primary reservoir of the first medicament 16.

The medicated module and the non-medicated module described herein should be designed to operate in conjunction with a multiple use injection device or family of devices, preferably a pen-type multi-dose injection device, similar to what is illustrated in FIG. 9. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose, but in either case it is a multi-dose device.

A typical injection device contains a cartridge or other reservoir of medication as described above. This cartridge is typically cylindrical in shape and is usually manufactured in glass. The cartridge is sealed at one end with a rubber bung and at the other end by a rubber septum. The injection pen is designed to deliver multiple injections. The delivery mechanism is typically powered by a manual action of the user, however, the injection mechanism may also be powered by other means such as a spring, compressed gas or electrical energy.

During injection, the needle guard 90 is moved in the proximal direction 110 against a force created by the elastic member 70. As the needle guard 90 moves proximally, its outwardly directed arms 96, 98 slide internally within the second cavity 62 of the outer body 52 from the distal groove 65 to the proximal groove 66. Once the outwardly directed arms 96 reach the proximal groove 66, the outwardly directed arms 96 pick up the movable locking feature 68. The first and second medicament 16, 38 may then be injected into an injection site by way of the second needle 80.

After injection, the drug delivery device 12 and the medicated module 10 are removed from the injection site, the needle guard 90 under the force of the biasing element 70 is forced in the distal direction 120. On being forced down or in the distal direction (represented by arrow 120 in FIG. 3) by the force created by the element 70, the needle guard 90 pulls the movable locking feature 68 into the distal groove 65 to thereby lock the needle guard 90 in the down position.

Locking the needle guard 90 in the down position in this manner provides a number of beneficial features. First, it prevents a user from re-using a non-sterile medicated module. Second, the locked needle guard 90 protects and substantially conceals the second needle 80 and, therefore, reduces the risk of a potential inadvertent needle stick. And third, in substantially concealing the second needle 80, the locked needle guard 90 acts to reduce any potential needle fear, needle phobia or needle anxiety that a patient may experience.

In the arrangements described herein, the second medicament 38 may be either in a powdered solid state, any fluid state contained within the secondary reservoir or capsule, or coated to the inside surface of the drug dispense interface. The greater concentration of the solid form of the medicament 38 has the benefit of occupying a smaller volume than the liquid having lower concentration. This in turn reduces the ullage of the medicated module 10. An additional benefit is that the solid form of the second medicament 38 is potentially more straightforward to seal in the secondary reservoir than a liquid form of the medicament 38. The drug delivery device 12 would be used in the same manner as the preferred embodiment with the second medicament 38 being dissolved by the first medicament 16 during dispense.

The shape of the medicated module 10 may be a cylindrical body or any other geometric shape suitable for defining a fluid reservoir or for containing discrete self-contained reservoir of the secondary medicament 38 and for attaching one or more needle cannula. The reservoir 36 in the medicated module 10 can be manufactured from glass or other drug contact suitable material. The integrated injection needle 40, 80 can be any needle cannula suitable for subcutaneous or intramuscular injection.

Preferably, the medicated module 10 is provided by a manufacturer as a stand-alone and separate assembly that is sealed to preserve sterility. The sterile seal of the module 10 is preferably designed to be opened automatically, e.g. by cutting, tearing or peeling, when the medicated module 10 is advanced or attached to the drug delivery device 12 by the user. This opening of the seal may be assisted by features such as angled surfaces on the end of the injection device or features inside the module 10.

Alternatively, the medicated module 10 may be provided in a kit form along where such a kit comprises at least one non-medicated module or a safety needle assembly. There are a number of reasons to provide one or more non-medicated needle assemblies along with a medicated module (such as illustrated in FIG. 1) in a kit form.

For example, there may be a situation where a patient may need to split a dose or top up a dose between two or more drug delivery devices. For example, there may be a situation where a user may need to administer a dose greater than the medicament remaining in the cartridge of the drug delivery device. As just one example, consider that a user might face a situation where they may need to administer a 50 unit dose and have only 30 units remaining in the cartridge of their old (i.e. part-used) drug delivery device. In such a situation, the user would first mount the medicated module onto the drug delivery, set the drug delivery device to administer 30 units of the first medicament and then administer the first and the second medicament in a generally known way. Then, because the user would still need to deliver the remaining 20 units of the first medicament, rather than use another medicated module containing a dose of the second medicament, the user would simply mount a non-medicated module to a new drug delivery device and then administer the remaining 20 units of the first medicament.

A user may also be faced with administering a large dose of the first medicament and may, for one reason or another, want to split this large dose (i.e., a large volume of medicament) into two or more injections. For example, some users may face themselves administering large doses on the order of 100 units or more of a single medicament for a single injection. Rather than administering such a large volume of medicament during a single injection, the user may administer 60 units first while using the medicated module and then administer the remaining 40 units using a non-medicated module. Splitting up the volume of the administered dose may help to reduce patient discomfort and may reduce potential medicament pooling under the skin. Splitting such a large dose may also be required where there is a mechanical restraint on the drug delivery device in that the device may not be mechanically capable of setting and administering such a large volume of medication.

Another reason that a user may need to split a dose between a medicated and a non-medicated module is that perhaps a physician has instructed a user to split a dose up into two or more injections. Two or more injections may be required if a user experiences certain negative reactions when administering a full dose of a first medicament simultaneously with a second medicated dose. Alternatively, the patient may be instructed to initially administer a first medicament during a specific time of day (e.g., a long-acting insulin in the morning) and then later in the day instructed to administer a combination of a first and second medicament (e.g., a long-acting insulin in combination with a short-acting insulin later in the day). In such a scenario, the non-medicated module could be used to administer the first injection.

Figure 5:
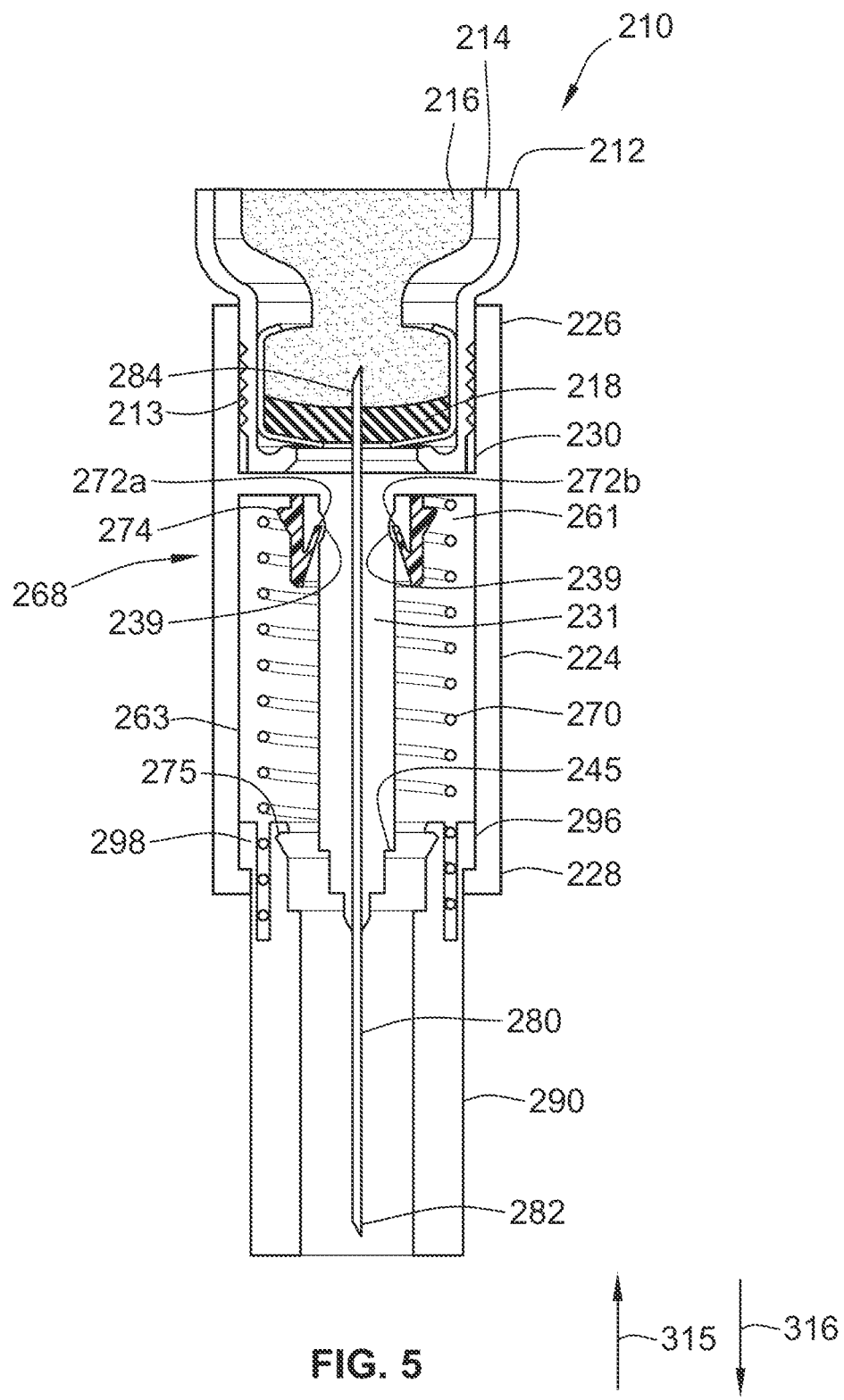
FIG. 5 illustrates a non-medicated module that may be provided in a drug delivery kit that includes the medicated module illustrated in FIG. 1.

FIG. 5 illustrates a first arrangement of a non-medicated module and is somewhat similar in construction to the medicated module 10. For example, this non-medicated module 210 comprises a connecting body 224, a double ended needle 280, a biasing member 270, a movable locking member 268, and a needle guard 290.

The connecting body 224 of the module 210 extends from a proximal end 226 to a distal end 228. The proximal end of the connecting body 224 is provided with a connector 230 (not shown) so that the connecting body 224 may be connected to the drug delivery device 212. Preferably, this connector 230 is provided along an inner surface 222 of the connecting body 224 and provides a releasable connection to the drug delivery device 212. Such a releasable connector 230 may comprise a snap fit, form fit, snap lock, luer lock or other similar connection mechanism known to those of skill in the art.

The connecting body 224 further comprises an injection needle 280 rigidly affixed within a main stem 231 of a needle hub. Preferably, this needle 280 comprises a double ended needle having a first piercing end 282 (e.g. a distal end) and a second piercing end 284 (e.g. a proximal end). In this preferred arrangement, when the module 210 is initially mounted to the drug delivery device 212 as illustrated in FIG. 5, the second piercing end 284 pierces the membrane 218 of the cartridge 214.

The connecting body 224 further comprises a first inner cavity 261. Preferably, the first inner cavity 261 is formed to contain the movable locking member 268 and a biasing member 270, such as a compression spring. As illustrated in FIG. 5, in the initial mounted position of the needle assembly, the biasing member 270 is in an extended state.

Figure 6:
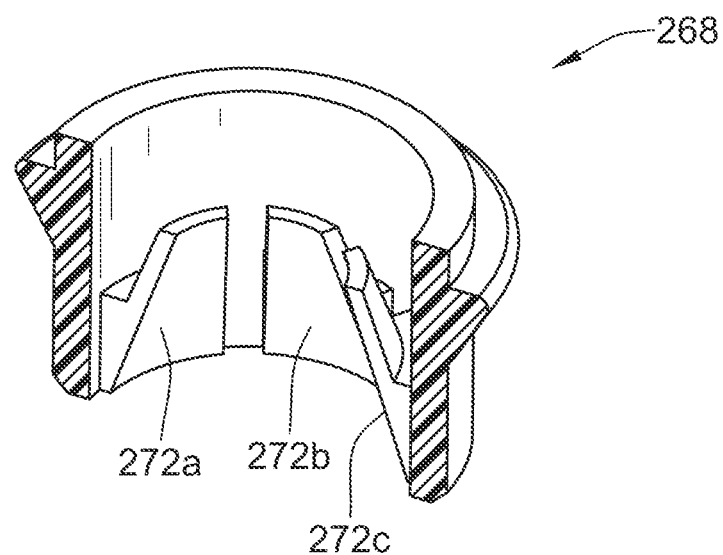
FIG. 6 illustrates a partial view of a movable locking member of the non-medicated module illustrated in FIG. 5.
Figure 7:
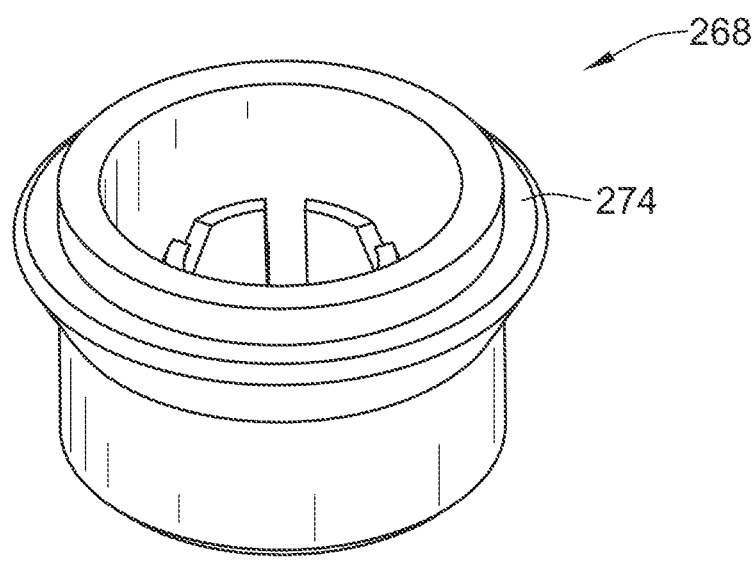
FIG. 7 illustrates a perspective view of the movable locking member illustrated in FIG. 6.

Details of a preferred arrangement of a locking mechanism can be clearly seen from FIGS. 6 and 7. FIG. 6 illustrates a cross sectional view of the movable locking member 268 and FIG. 7 illustrates a perspective view of the locking member 268. As illustrated, the movable locking member 268 is preferably in the form of a cylindrical shaped member having an outer beveled edge 274. Preferably, the locking member 268 comprises a plurality of annular spring fingers 272 a, b, c within the cavity created by the locking member 268. As illustrated in the first mounted position of FIG. 5, these spring fingers 272 a, b, c engage a recess 239 located on the proximal end 226 of a main stem 237 (see FIG. 8) of the connecting body main hub. The engagement of the spring fingers 272 *a, b, c* and the recess 239 prevents the locking member 268 from moving in the distal direction prior to injection. This movable locking member 268 is used to lock out the needle guard 290 after an injection has been made. That is, after the needle guard 290 is first moved in a proximal direction and then returned in a distal direction under the force of the biasing member 270.

In this preferred arrangement, when the needle assembly 210 is initially mounted to the drug delivery device 212, the second piercing end 284 of the needle 280 pierces the membrane 218 of the cartridge 214 contained in the drug delivery device 212. The first piercing end 282 of the needle 280 is illustrated as being substantially concealed from a user's view by way of the needle guard 290. Concealing the needle 280 helps to reduce needle anxiety that a patient may be experiencing while also reducing a potential inadvertent needle stick.

Preferably, the needle guard 290 comprises a tubular shaped element and, in a relaxed position, as illustrated in FIG. 5, substantially conceals the needle 280. While substantially concealing this needle 280, the needle guard 290 also helps to prevent inadvertent needle sticks. In FIG. 5, this needle guard 290 is illustrated in an unlocked position. That is, during an injection step where a user initiates the injection, the needle guard 290 is free to be moved in a proximal direction or towards the drug delivery device 212. Preferably, the needle guard 290 comprises outwardly directed arms 296, 298 that are in sliding engagement with an inner surface 263 of the inner cavity 261 of the connecting body 224.

As illustrated in FIG. 5, the module 210 is shown in a first mounted position on the drug delivery device 212. In this first position, the connecting body 224 is connected to a distal end of the drug delivery device 212. As illustrated, the drug delivery device 212 comprises threads 213 for engagement with the connecting body 224. In one arrangement, the connecting body 224 may comprise a threaded connector 230 to releasably engage these threads. However, in an alternative arrangement, the connecting body 224 may comprise a connector 230 comprising a form fit or snap fit arrangement or the like. In this manner, the module 210 may be connected to the drug delivery device 212 merely by sliding the module 210 onto the distal end of the drug delivery device 212.

In this initial mounting position, the needle 280 is in fluid communication with the medicament 216 contained in the cartridge 214. Where the drug delivery device 212 comprises a dose setter, a dose of the drug delivery device 212 may then be set using a dose setter 8 (see FIG. 9) in the normal manner (e.g., by dialing out the appropriate number of units). Dispense of the medicament 216 may be achieved by subcutaneously injecting the medicament 216 via activation of a dose button on device 212. The dose button may be any triggering mechanism that causes the dose of the medicament that was set by the dose setter to move distally towards the distal end of the device. In a preferred embodiment, the dose button is operably connected to a spindle that engages a piston in the cartridge 214.

During injection, the needle guard 290 is moved in a proximal direction 315 against a force created by the biasing member 270. As the needle guard 290 moves proximally, its arms 296, 298 slide internally within the cavity 261 of the connecting body 224. Once the needle guard beveled edge 275 reaches the rib 274, the beveled edge 275 slips around the rib 274 so that the needle guard 290 picks up the movable locking member 268. The medicament 216 may then be injected into an injection site by way of the needle 280.

After the injection, the drug delivery device 212 and the module 210 are moved away from the injection site. Then, under the force of the biasing member 270, the needle guard 290 is forced in the distal direction 316. On being forced down or in the distal direction 316 by the force created by the biasing member 270, the needle guard 290 pulls the movable locking member 268 distally.

Figure 8:
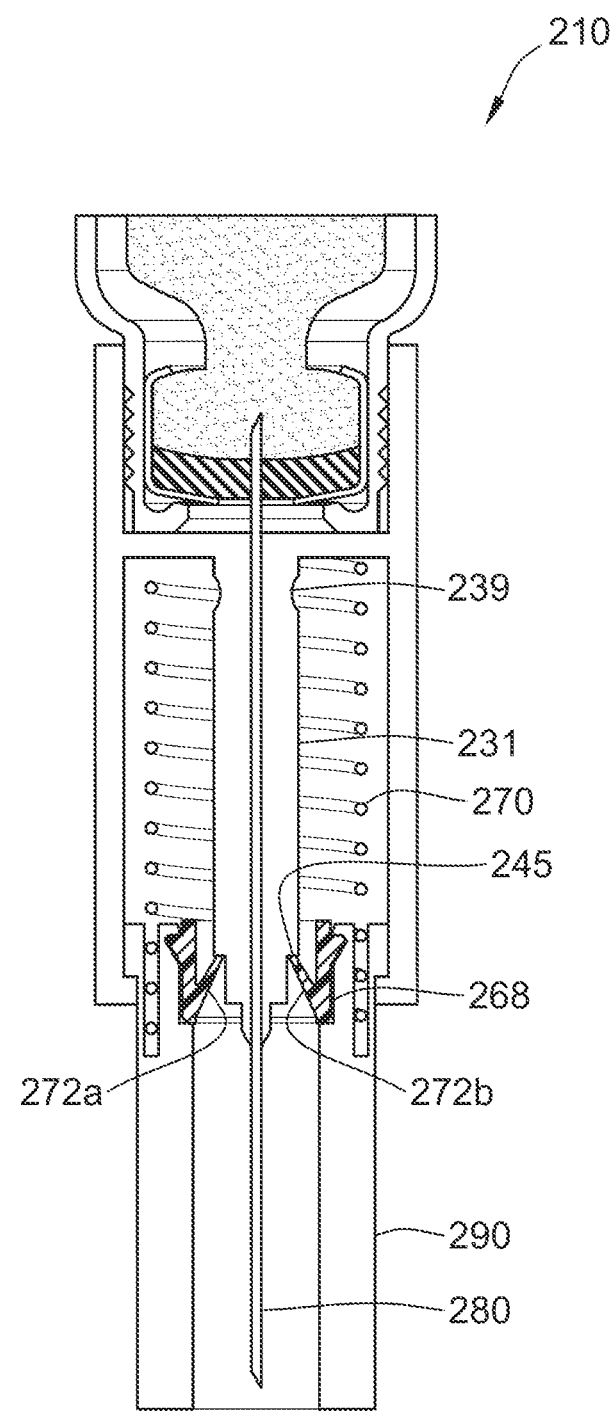
FIG. 8 illustrates a front view of the module illustrated in FIG. 5 having a locked needle guard.

FIG. 8 illustrates the module 210 with the needle guard 290 in a locked position. As illustrated, the annular ring fingers 272 *a, b, c* of the locking member 268 flex inwardly to as to reside along a first recess 245 provided along the distal end of the main stem 231.

As such, the annular ring fingers 272 prevent the needle guard 290 from moving in the proximal direction and, therefore, prevent a user from re-using the module 210.

Locking the needle guard 290 in the down position in this manner provides a number of beneficial features. First, it prevents the user from re-using a non-sterile medicated module. Second, the locked needle guard 290 protects and substantially conceals the needle 280 and, therefore, reduces the risk of a potential inadvertent needle stick. In addition, by substantially concealing the needle 280, the locked needle guard 290 acts to reduce any potential needle fear, needle phobia or needle anxiety that a patient may experience.

As discussed above with respect to FIG. 1, the medicated module 10 is shown in a first mounted position on the drug delivery device 12. In this first position, the connecting body 24 is connected to a distal end of the drug delivery device 12. As illustrated in this arrangement, the drug delivery device 12 comprises a conventional thread arrangement 13 for engagement with the connecting body 24. However, in an alternative arrangement, the connecting body 24 may comprise a connector 30 comprising a form fit or snap fit connector arrangement or the like. In this manner, the medicated module 10 may be connected to the drug delivery device 12 merely by sliding the medicated module 10 onto the distal end of the drug delivery device 12.

The connection or attachment between the medicated module 10 (illustrated in FIGS. 1-4) as well as the non-medicated module 210 (illustrated in FIGS. 5-8) may contain additional features, such as connectors, stops, splines, ribs, grooves, and the other similar mechanical design features, that ensure that only a specific medicated module 10 or non-medicated module 210 is attachable to a complementary drug delivery device. That is, the specific needle assembly (i.e. a medicated module or a non-medicated module) could comprise certain mechanical features that are dedicated to work with only a specific/complementary dedicated drug delivery device. Such additional features would prevent the insertion of a non-appropriate medicated module to a non-matching injection device, such as a drug delivery device comprising a conventional coupling mechanism. In one preferred arrangement, the additional features, such as connectors, stops, splines, ribs, grooves, and the like mechanical design features may be integral to either the needle assembly or the drug delivery device or both. Alternatively, these additional features, such as connectors, stops, splines, ribs, grooves, and the like mechanical design features may be provided as an independent part or collection of parts that allow the needle assembly to properly interface with a conventional drug delivery device, such as the device illustrated in FIG. 9.

Figure 10:
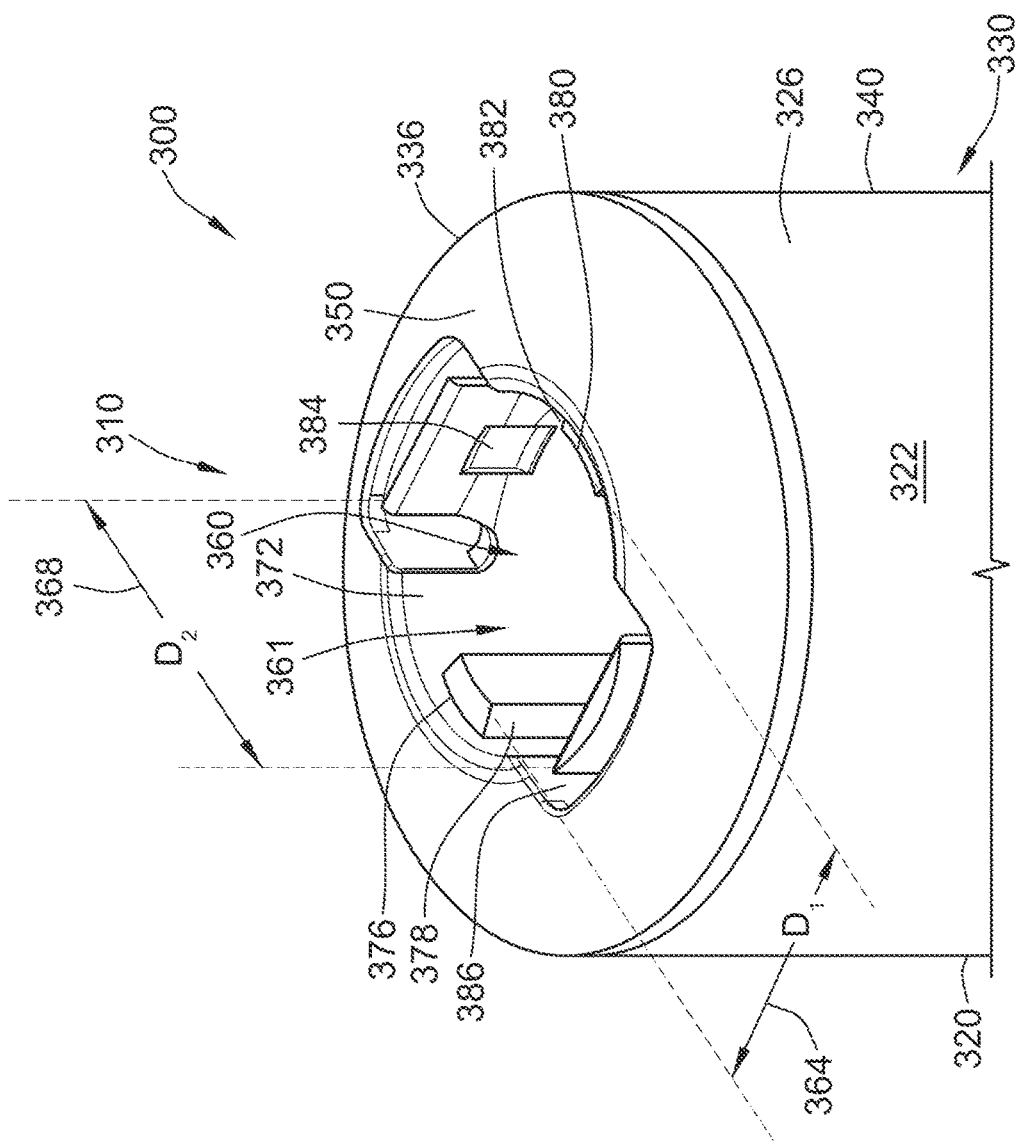
FIG. 10 illustrates a perspective view of one arrangement of a dedicated needle assembly configured to be attachable to a dedicated drug delivery device.

FIG. 10 illustrates one example of such an additional feature in the form of a dedicated mechanical coupling 310 that can be used to dedicate a needle assembly 300, such as a medicated module, to a corresponding dedicated drug delivery device. As such, FIG. 10 illustrates a perspective view of a first arrangement of the dedicated needle assembly 300 comprising the dedicated mechanical coupling 310.

The dedicated mechanical coupling 310 in this arrangement is integral with the dedicated needle assembly 300. For example, the needle assembly 300 could take the form of the medicated module 10 illustrated in FIG. 1 while replacing the threaded connector 30 with the dedicated mechanical coupling 310. However, in an alternative arrangement, the dedicated mechanical coupling 310 may comprise a separate component that may then be used to mate the medicated module 10 illustrated in FIG. 1 to the drug delivery device.

By dedicated needle assembly, it is meant that the needle assembly 300 can only be properly mechanically coupled to a dedicated drug delivery device that is mechanically configured to administer a dose of medicament from a cartridge contained within the dedicated drug delivery device and cannot be used to properly administer a dose of a drug contained in an device that does not have the proper dedicated mechanical coupling.

In one preferred arrangement, this needle assembly 300 may comprise a medicated module, such as the medicated module 10 illustrated in FIG. 1. Alternatively, this needle assembly 300 may comprise a needle assembly that does not comprise a medicament, such as the non-medicated module 210 illustrated in FIG. 5. In yet another alternative arrangement, the needle assembly 300 may comprise a double ended needle assembly such as a conventional needle assembly 600 illustrated in FIG. 20. In this alternative arrangement, an internal thread of this double ended needle assembly is replaced with the proposed dedicated mechanical coupling 310. However, as those of skill in the relevant art will recognize, the presently described, illustrated, and claimed dedicated needle assemblies may be used for other attachment arrangements, systems and arrangements comprising alternative dedicated mechanical couplings.

Returning to FIG. 10, the dedicated needle assembly 300 comprises an outer connecting body 320 and this body may define a generally cylindrical shape 322. This outer connecting body 320 extends from a distal end 330 to a proximal end 336 of the needle assembly 300. An outer surface 340 of this connecting body 320 may comprise a generally smooth outer surface 326. An advantage of such a smooth surface 326 is that it provides an area to provide a label or other similar source or contents identifier so that a user can identify the medicament contained within the needle assembly (if a medicament is provided, e.g. in case that the needle assembly comprises a medicated module).

The outer connecting body 320 further comprises a generally smooth proximal end surface 350 wherein this proximal end surface 350 is mechanically configured to define an engaging cavity 360. One advantage of such a generally smooth proximal end surface 350 is that such a surface tends to reduce interference during the insertion of the drug delivery device and may also be used as an additional identifier of the contents/strength or concentration of the drug about to be attached to the drug delivery device. The engaging cavity 360 may have a generally circular shaped opening 361 and may be defined to essentially comprise two different engagement cavity diameters: a first engaging cavity diameter D1 364 and a second engaging cavity diameter D2 368. The second engaging cavity diameter D2 368 is larger or wider than first engaging cavity diameter D1 364. As will be explained in greater detail below, various mechanical elements that are provided along an inner wall 372 of this engaging cavity 360 are mechanically coded to receive a similarly dedicated distal end of a drug delivery device, similar to the drug delivery device 1 illustrated in FIG. 9.

However, the conventional threaded distal end of the drug delivery device 1 illustrated in FIG. 9 will need to be modified to comprise a corresponding dedicated coupling mechanism that is coded to properly cooperate with the various mechanical elements of the engaging cavity 360. As just one example, the threaded distal end of this drug delivery device 1 can be altered by modifying the distal end of the cartridge so as to comprise a dedicated mechanical coupling.

Alternatively, the conventional threaded distal end of the drug delivery device 1 can receive a separate component part that comprises the dedicated mechanical coupling. In such an arrangement, this separate component part is first coupled onto the distal end of the drug delivery device 1 (e.g., rotated onto the conventional threaded distal end). Then, the distal end of the device 1 having the separate component part is then inserted into the engaging cavity 360. One advantage of utilizing such a separate component part is that the drug delivery device 1 used in such a dedicated needle assembly system may comprise a conventional threaded distal portion and will not need to be altered or modified. Such a dedicated needle assembly system can save production, manufacturing and storage costs that can necessary arise by having to manufacture and transport a large number of different drug delivery devices so as to provide the desired medicament and drug delivery device differentiation. This separate component part may be a releasably engaged or permanently attached at the point of manufacture. This would allow retrofitting of the dedicated features to an already established commercially available device. The latter action would help to ensure dedication by fixing the separate component part to the delivery device such that the user could not easily remove it, thus creating a dedicated delivery device without significant impact on an existing assembly line. The separate component part would simply be added as an additional component and could be added in a single extra assembly step.

Returning to FIG. 10, the first engaging cavity diameter D1 364 has a diameter that is sized to be smaller than an outer diameter of a standard or a conventional Type A needle assembly. For example, comparing the needle assembly 300 in FIG. 10 with the conventional double ended needle assembly 600 illustrated in FIG. 20, the first engaging cavity diameter D1 364 comprises a diameter that is smaller than an outer diameter DType A 620 of the standard or conventional Type A threaded/cartridge holder interface illustrated in FIG. 9. As such, a user is prevented from attaching the dedicated needle assembly 300 to a non-approved primary drug delivery device, such as the conventional device 1 illustrated in FIG. 9.

Returning to FIG. 10, the engaging cavity 360 comprises an inner wall 372 located within the outer connecting body 320. A first and a second tongue or protrusion 376, 380 is provided along the inner wall 372. The first and second protrusions 376, 380 are 180 degrees offset from one another and situated across the first inner diameter D1 364. In addition, the engaging cavity 360 further comprises two recess features 384, 386 (only one of these two recess features 384 is illustrated in FIG. 10) which are also provided along the inner wall 372. These recess features 384, 386 are also 180 degrees offset from one another and are situated across, in particular in line with, the second inner diameter D2 368.

Figure 11:
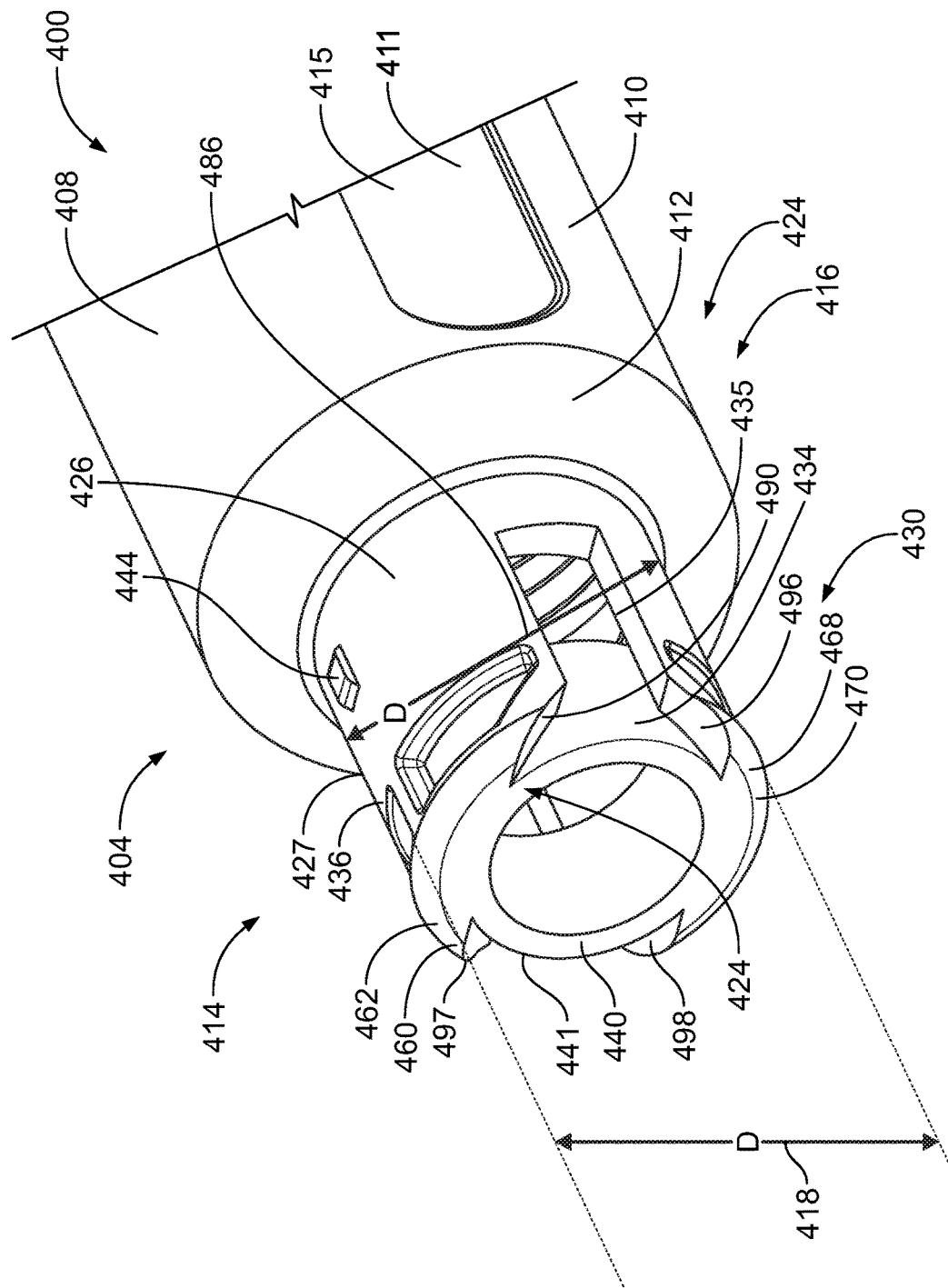
FIG. 11 illustrates a perspective view of a distal end of one arrangement of a dedicated drug delivery device that is configured to be attachable to the dedicated needle assembly illustrated FIG. 10.

FIG. 11 illustrates a distal end 404 of a dedicated drug delivery device 400 that is mechanically coded for use with a dedicated needle assembly, such as the dedicated needle assembly 300 illustrated in FIG. 10. In one preferred arrangement, this dedicated drug delivery device 400 may be operated by a user to select a dose of a medicament and then administer this selected medicament dose in a similar fashion as the convention drug delivery 1 illustrated in FIG. 9. However, although the general mechanical operation between the two devices might be the same or similar, the distal end 404 of the dedicated drug delivery device 400 will comprise a modified distal end 404. With such a modified distal end 404, the dedicated drug delivery device 400 can only be mechanically and properly operatively connected to the dedicated needle assembly 300 illustrated in FIG. 10.

FIG. 11 illustrates only a portion of the dedicated drug delivery device 400 and illustrates a distal portion 408 of the dedicated cartridge holder 410 and a distal end 404 of the drug delivery device 400. The dedicated cartridge holder 410 is one possible embodiment of the previously mentioned dedicated coupling member. The dedicated cartridge holder 410 houses or contains a cartridge or ampoule 411 and this cartridge 411 contains a medicament 415, such as a long-acting insulin or a short-acting insulin. In one arrangement, the cartridge holder 410 may comprise a disposable cartridge holder. Alternatively, the cartridge holder 410 may comprise a reusable cartridge holder. By disposable cartridge holder, it is meant the cartridge holder may be obtained from the manufacturer preloaded with the cartridge 411 containing the medicament 415 and cartridge holder 410 cannot be reloaded with new medicament (i.e., a new cartridge) after the initial medicament 415 is exhausted. A reusable cartridge holder 410 can allow the user to reload the holder with new medicament (i.e., a new cartridge).

As can be seen in FIG. 11, the distal end 404 of the dedicated drug delivery device 400 does not comprise a conventional threaded distal end (as the drug delivery device illustrated FIG. 1). Rather, the distal end 404 comprises a dedicated mechanical coupling 414. This mechanical coupling 414 may be integral with the dedicated cartridge holder 410 (as illustrated in FIG. 11). That is, the dedicated cartridge holder 410 along with the dedicated mechanical coupling 414 may be manufactured or molded as one integral component. Alternatively, the mechanical coupling 414 may comprise a separate component that can be attached to a threaded distal end of a conventional drug delivery device, such as the device 1 illustrated in FIG. 9. This alternative non-integral mechanical coupling arrangement is discussed in detail herein below with respect to FIGS. 17-19.

In a first arrangement, the illustrated dedicated mechanical coupling 414 comprises a generally cylindrical extension 416. This extension 416 extends from an extension proximal end 424 that is located near the cartridge holder 410 to an extension distal end 430. This generally cylindrical extension 416 comprises a generally smooth first body portion 426 and a second body portion 436. The overall length of the first body portion 426 and the second body portion 436 can vary based on a depth of a complementary engaging cavity of a needle assembly, such as the engaging cavity 360 of needle assembly 300. However, in this illustrated arrangement, an overall length of the extension 416 can be selected so as to be properly inserted into the engaging cavity 360 of the needle assembly 300. The proximal end 424 may be located near a shoulder 412 of the cartridge holder 410 of the generally cylindrical extension 416.

As illustrated in FIG. 11, the first body portion 426 of the generally cylindrical extension 416 extends from the proximal end towards the distal end of the generally cylindrical extension 416. The first body portion 426 comprises a generally smooth outer surface 427 and has an inner diameter Dinner 486.

Figure 15:
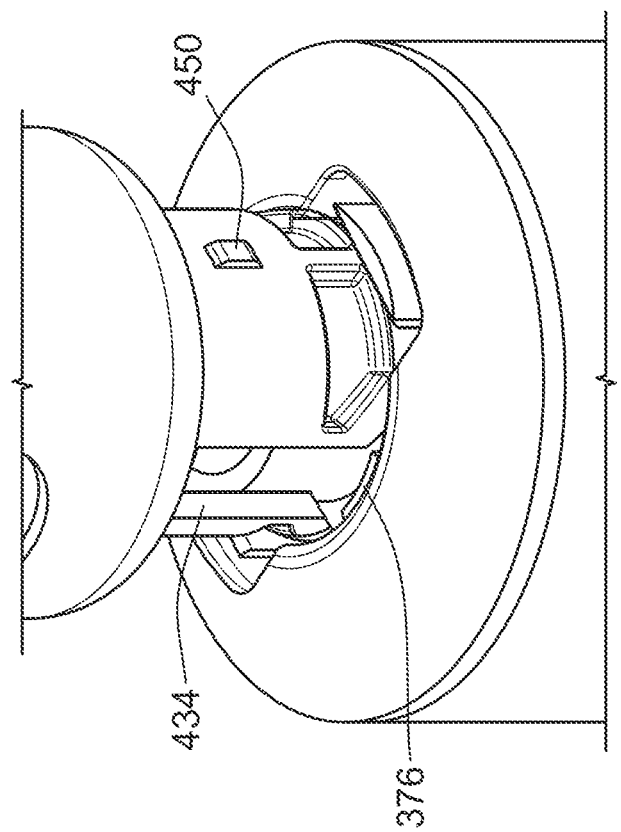
FIG. 15 illustrates close-up view of the dedicated drug delivery device after the device has been rotated to align its dedicated mechanical coupling with that of the dedicated needle assembly illustrated FIG. 10.
Figure 14:
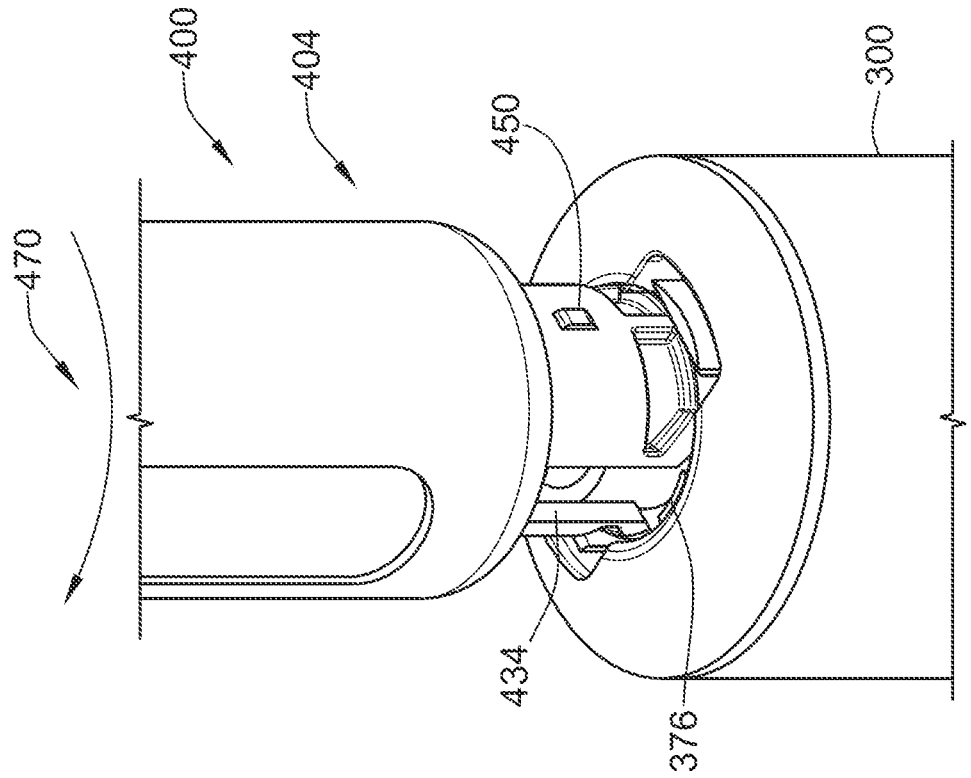
FIG. 14 illustrates a perspective view of the dedicated drug delivery device after the device has been rotated to align its dedicated mechanical coupling with that of the dedicated needle assembly illustrated FIG. 10.

In one preferred arrangement, a plurality of bump features are provided along the outer surface 427. For example, in one illustrative arrangement, two bump features 444, 450 are positioned along the outer surface 427 and are preferably positioned 180 degrees apart from one another (the second bump feature 450 is illustrated in FIGS. 14-15). As illustrated, these bump features 444, 450 may be positioned along the cylindrical extension 416 so that when the dedicated mechanical coupling 414 is fully inserted into the engaging cavity 360 of the needle assembly 300, the first and second bump features 444, 450 interact or mate with the first and second recess features 384, 386, respectively. In one preferred arrangement, when a user properly inserts the distal end 404 of the drug delivery device 400 into the needle assembly 300 (FIG. 10), the interaction between the first and second bump features 444, 450 and the first and second recess features 384, 386 will provide a tactile and/or audible confirmation that the two components have been properly connected.

One advantage of such a dedicated coupling mechanism is that it can provide both tactile and audio feedback to a user on full fitment provided by axially engaged bump features on the dedicated coupling member, e.g. on the cartridge holder, clicking into recess features on the dedicated needle assembly, e.g. on the medicated module. As those of skill in the art will recognize, alternative bump and ridge arrangements could also be utilized. As just one example, these features could be reversed where the bump features may be provided by the needle assembly and the recess features may be provided by the distal end of the drug delivery device.

The dedicated mechanical coupling 414 further comprises a first and a second upstand feature 460, 468. These upstand features 460, 468 may be located along a second body portion 436 of the cylindrical extension 416 and may extend from the proximal end 424 towards the distal end 430 of the cylindrical extension 416. At a most distal end, first upstand feature 460 comprises a first lip 462 wherein this lip 462 flares radially outward away from the smooth outer surface 427 of the first body portion 426. Second upstand feature 468 comprises a similar lip 470 that also flares radially outward away from the smooth outer surface 427 of the first body portion 426. As such, the outer most radially directed portions of lips 462, 470 define an outer diameter DOuter 418 In one arrangement, this outer diameter DOuter 418 is larger (or wider) than the inner diameter Dinner 486 defined by the first body portion 426 of the cylindrical extension 426. In a preferred arrangement, this outer diameter DOuter 418 will be larger (or wider) than a diameter of a standard "Type A" screw thread needle assembly, such as the inner diameter DType A 620 of the conventional Type A double ended screw thread needle assembly illustrated in FIG. 20. As such, a user will be prevented from attaching a conventional Type A double ended needle assembly 600 to the distal end 404 of the dedicated drug delivery device 400.

The dedicated mechanical coupling 414 further comprises a first and a second groove 434, 440. In one preferred groove arrangement, the first and second grooves 434, 440 are positioned 180 degrees apart from each other. Preferably, each groove 434, 440 defines a certain width. For example, first groove 434 may define a first width 435 and second groove 440 may define a second width 441. The first width 435 of the first groove 434 may or may not be equivalent to the second width 441 of the second groove 440. In one preferred arrangement, the first and second widths 435, 441 are generally equivalent. If the widths or rotational positioning of the ribs were to differ, this may be one such way the dedicated features could be coded within a family of different dedicated needle assemblies.

As illustrated, these groove widths 435, 441 may be generally equivalent to a width 378, 382 of the protrusions 376, 380 provided along the inner wall of the engaging cavity 360. For example, the first width 435 of the first groove 434 may be generally equivalent to the first width 378 of the first protrusion 376. Similarly, the width 441 of the second groove 440 may be generally equivalent to the width 382 of the second protrusion 380 of the dedicated needle assembly 300.

In addition, the dedicated mechanical coupling 414 may further comprise a first and a second chamfered edge 490, 496 provided near the distal opening of the first groove 434. The second groove 440 comprises a similar chamfer edge arrangement 497, 498. As discussed in greater detail below, one advantage of such a chamfered edge arrangement is that when inserting the distal end of cartridge holder into the needle assembly 300, these chamfer edges aid to guide the grooves 434, 440 into proper alignment with the receiving protrusions 376, 380.

FIG. 12 illustrates a perspective view of the dedicated drug delivery device 400 illustrated in FIG. 11 just prior to being inserted into the engaging cavity 360 of the dedicated needle assembly 300 illustrated in FIG. 10 where the distal end of the device 400 is initially not aligned with the engaging cavity 360. Ordinarily, to insert the dedicated cartridge holder 410 into this needle assembly 300, a user will typically hold the needle assembly 300 in one hand while holding the drug delivery device 400 in the other hand while inserting the distal end 404 into the engaging cavity 360. During insertion, when the grooves 434, 440 on the cartridge holder 410 properly align with the protrusions of the needle assembly 300, for which purpose the user had to rotate the needle assembly 300 of FIGS. 12 and 13 by 90 degrees prior to insertion into the cartridge holder 410, the distal end of the device 404 can be properly inserted. Ordinarily, this connection action will comprise a purely axial motion on the part of the user.

However, during the process of inserting the drug delivery device 400 into the needle assembly 300, there may be situations where the first and second grooves 434, 440 of the cartridge holder 410 do not align with the first and second protrusions 376, 380 of the receiving cavity 360. As just one example, FIG. 12 illustrates the situation where the protrusion and groove features are not properly aligned.

For example, FIG. 12 illustrates the distal end 404 of the drug delivery device 400 in a first position. In this first position, the distal end 404 of the device 400 attempts to enter the engaging cavity 360 in an axial direction. In this axial direction, initially, there is no rotation of the needle assembly 300 and no rotation of the drug delivery device 400. However, as illustrated in the close-up view provided in FIG. 13, the first groove 434 and the second groove 440 on the distal end 404 of the dedicated drug delivery device 400 are not properly aligned with the first protrusion 376 and second protrusion 380 of the engaging cavity 360, respectively.

Because the grooves 434, 440 of the cartridge holder 410 are not aligned with the protrusions 376, 380, the outer diameter DOuter 418 defined by the first and second upstand features 460, 468 is blocked by the protrusions 376, 380 because the outer diameter DOuter 418 is wider than the first inner diameter D1 364 defined by the engaging cavity 360. As such, the distal end 404 of the drug delivery device 400 is prevented from axially entering the engaging cavity 360. Therefore, either the needle assembly 300 or the drug delivery device 400 must be rotated in order for the outer diameter DOuter 418 to be aligned with the larger second engaging cavity diameter D2 368 and so as to align the protrusions 376, 380 and the grooves 434, 440.

FIG. 14 illustrates the situation where the protrusions 376, 380 and the grooves 434, 440 are now in alignment after the device 400 has been rotated in the direction of arrow 480 by approximately 90 degrees. As illustrated, when inserted into the dedicated needle assembly 300, the dedicated drug delivery device 400 will rotate so as to align the protrusions 376, 380 with the grooves 434, 440. Once there is coarse alignment between the distal end 404 and the engaging cavity 360 is achieved, the chamfered edges of the up stand features 460, 468 will tend to assist the user in guiding these component parts together into an accurately controlled rotational alignment.

FIG. 15 illustrates a close-up view of the dedicated drug delivery device 400 after the device 400 has been rotated in the clockwise direction shown by arrow 480 (FIG. 14) so as to align with the dedicated mechanical coupling 310 of the dedicated needle assembly 300 illustrated in FIG. 10. As can be seen from FIGS. 14 and 15, the first groove 434 is now in alignment with the first protrusion 376. Similarly, the wider diameter of DOuter 418 defined by the two up stand features 460, 468 is now also aligned with the larger diameter D2 368 of the engaging cavity 360. As the grooves 434, 440 and protrusions 376, 380 approach one another for a final alignment position, the chamfers on the first and second grooves 434, 440 will aid in mating the first groove 434 with the first protrusion 376.

FIG. 16 illustrates a perspective view of the distal end 404 of the dedicated drug delivery device 400 after it has been fully inserted into the dedicated needle assembly 300 illustrated in FIG. 10. The needle assembly 300 and device 400 are now ready to administer a dose of the medicament 415 contained within the properly attached cartridge 411 contained within the drug delivery device 400. After a dose has been set and then administered, a user merely needs to pull apart the two components to remove the dedicated needle assembly 300 from the dedicated drug delivery device 400. The retention feature between the dedicated needle assembly 300 and the dedicated drug delivery 400, in the illustrated arrangement, may be refined to optimise the forces required to attach and remove the needle assembly 300. As just one example, the flexible nature of the upstand features 460, 468 can be tuned to control this force to an acceptable level given various material selections. Similarly, the lead ins on each of the sides of the bump features 444, 450 can be tuned to result in different attachment and detachment forces should this be required.

Figure 17:
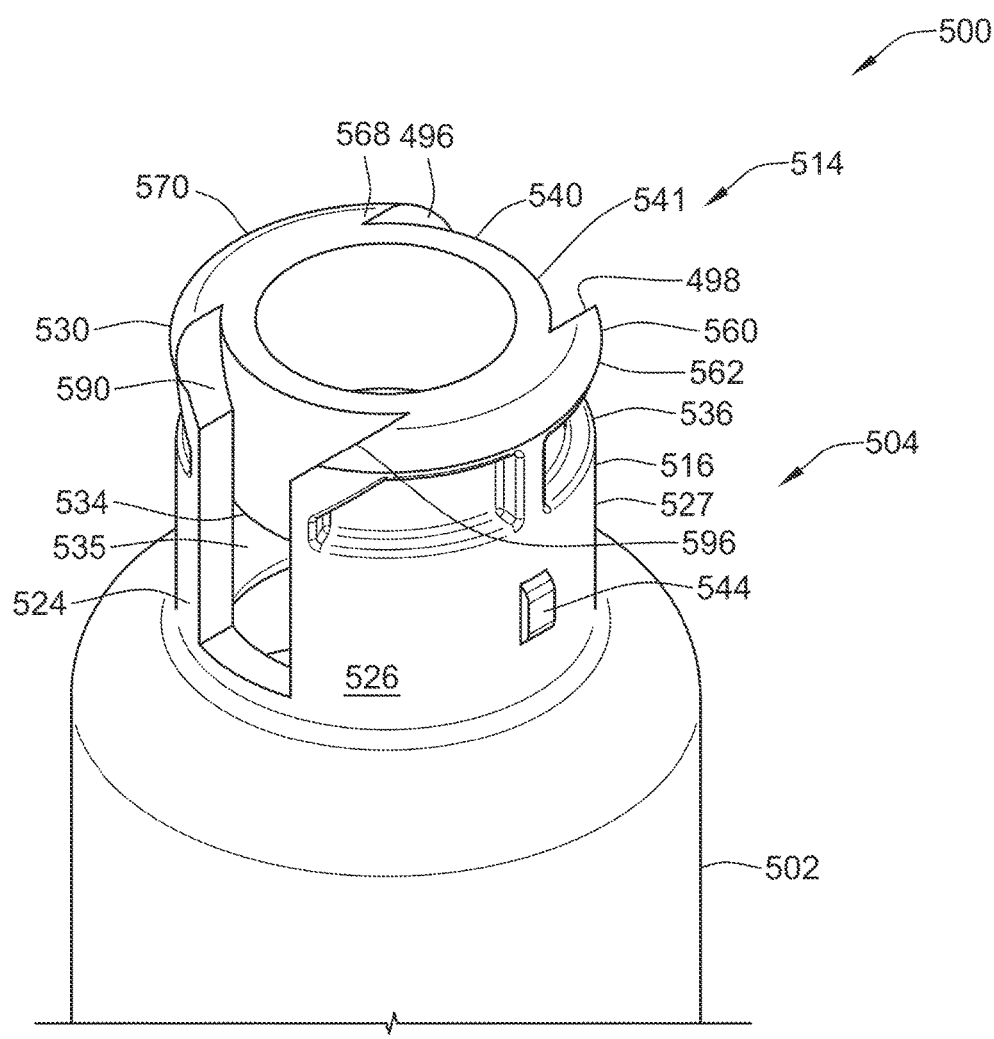
FIG. 17 illustrates a perspective view of one arrangement of a dedicated cap that may be used to connect a drug delivery device to the dedicated needle assembly illustrated FIG. 10.
Figure 18:
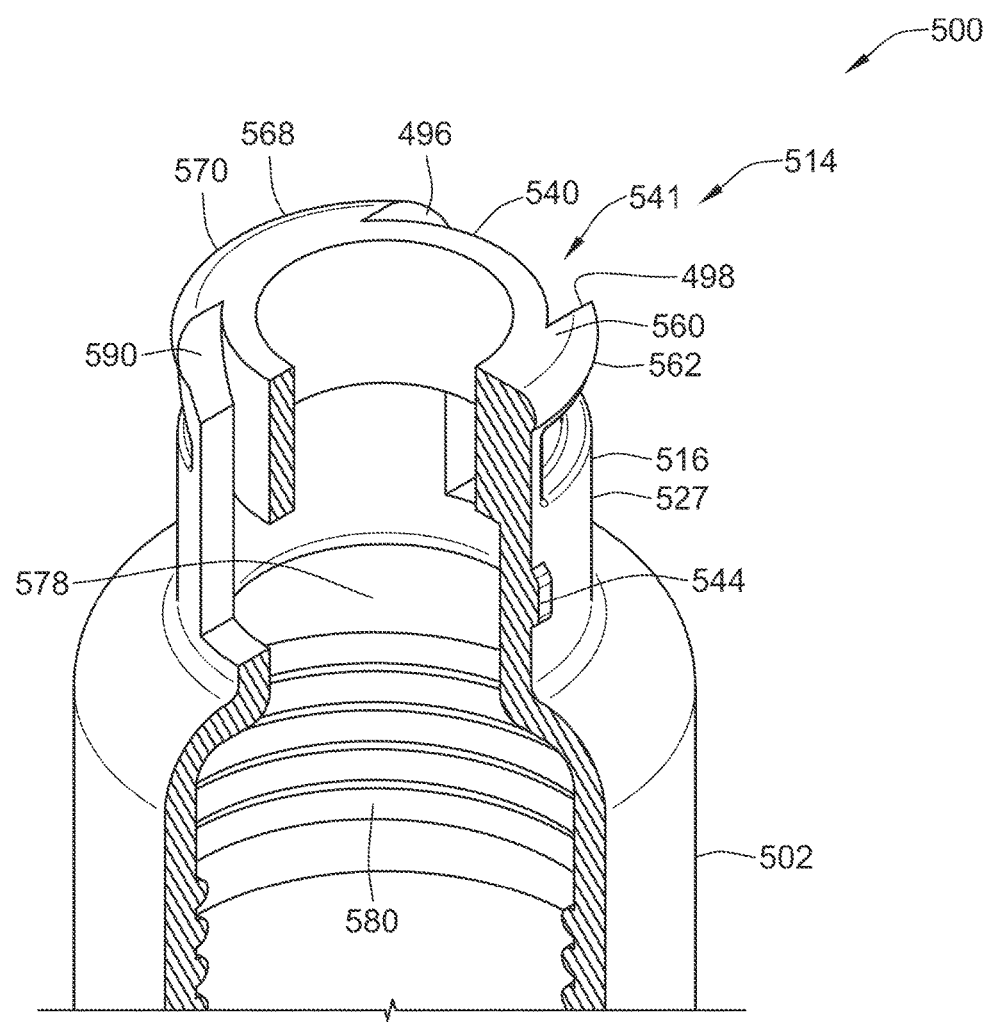
FIG. 18 illustrates a cut away view of the dedicated cap illustrated in FIG. 17.
Figure 19:
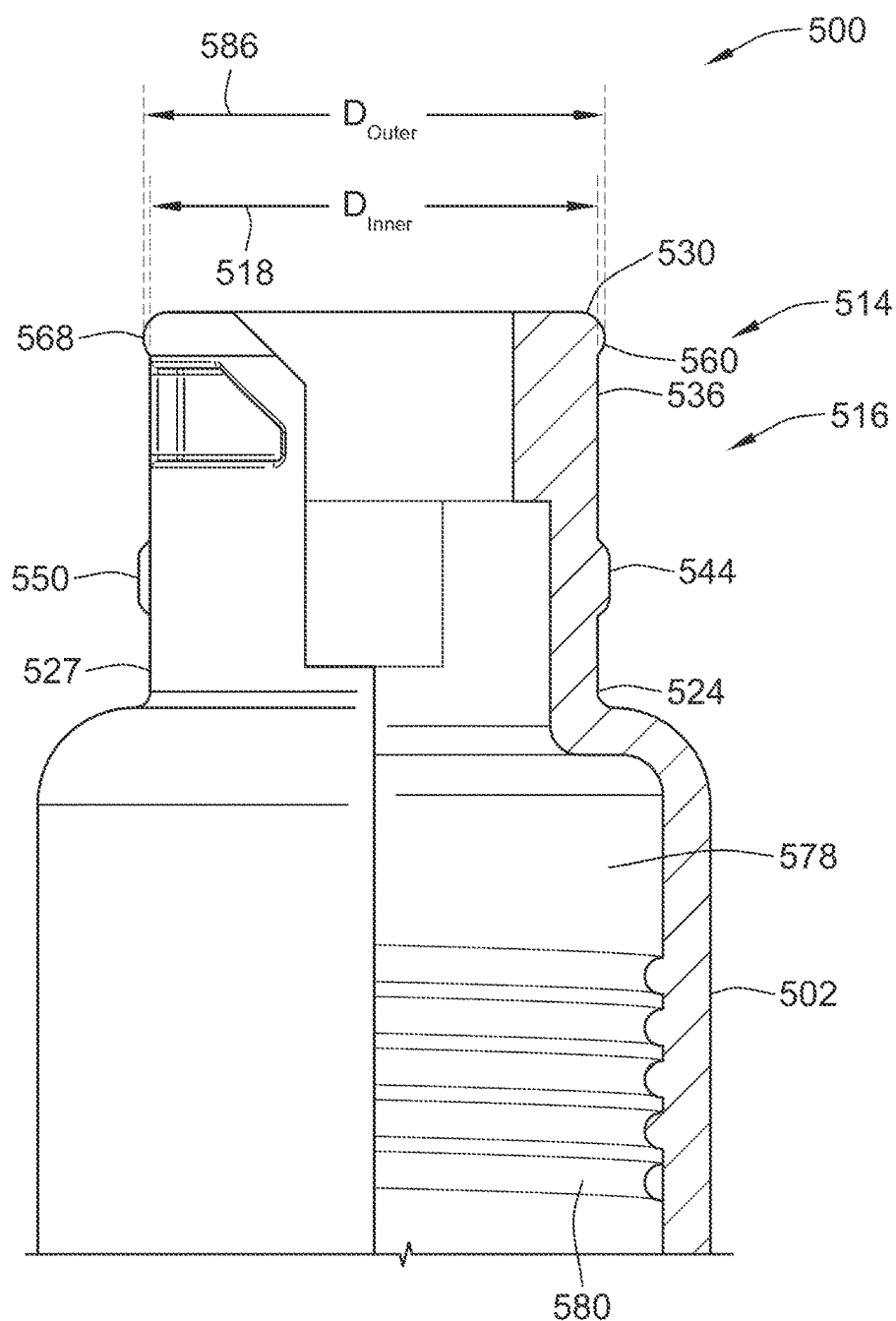
FIG. 19 illustrates a partial sectional view of the dedicated cap illustrated in FIG. 17.

The dedicated mechanical coupling 310 may be integral with the dedicated needle assembly 300. The dedicated mechanical coupling 414 may be integral with the dedicated drug delivery device 400 or, alternatively, the dedicated mechanical coupling 414 may comprise a separate component that is then used to interface between the medicated module, such as the medicated module 10 illustrated in FIG. 1, and the drug delivery device. For example, FIG. 17 illustrates a perspective view of one arrangement of a dedicated coupling member. According to this embodiment, the dedicated coupling member comprises a cap 500. Cap 500 that may be used to dedicate a drug delivery device to the dedicated needle assembly 300 illustrated in FIG. 10. FIG. 18 illustrates a cut away view of the dedicated cap 500 illustrated in FIG. 17 and FIG. 19 illustrates a partial sectional view of the dedicated cap 500 illustrated in FIG. 17. The dedicated cap 500 may act as an adapter connecting, for example, dedicated needle assembly 300 with non-dedicated drug delivery device.

Referring now to FIGS. 17-19, the dedicated cap 500 comprises a dedicated mechanical coupling 514 and this coupling 514 comprises similar features as the dedicated mechanical coupling 414 of the drug delivery device 400 illustrated in FIG. 11.

For example, FIG. 17 illustrates a perspective view of a distal end 504 of the dedicated cap 500 that is mechanically coded for use with a dedicated needle assembly, such as the dedicated needle assembly 300 illustrated in FIG. 10.

As can be seen from these Figures, the dedicated cap 500 comprises the dedicated mechanical coupling 514 comprising a main body 502 and a generally cylindrical extension 516 that extends from the main body 502. The cylindrical extension 516 extends from an extension proximal end 524 to an extension distal end 530. This generally cylindrical extension 516 comprises a generally smooth first body portion 526 and a second body portion 536. The overall length of the first body portion 526 and the second body portion 536 can vary based on a depth of a complementary engaging cavity of a needle assembly, such as the engaging cavity 360 of needle assembly 300. However, in this illustrated arrangement, an overall length of the extension 516 can be selected so as to be properly inserted into the engaging cavity 360 of the needle assembly 300.

As illustrated, the first body portion 526 of the generally cylindrical extension 516 extends from the proximal end towards the distal end of the generally cylindrical extension 516. The first body portion 526 comprises a first extension portion that comprises a generally smooth outer surface 527. This first extension portion 526 comprises an inner diameter Dinner 518 (illustrated in FIG. 19).

In one preferred arrangement, a plurality of bump features are provided along the outer surface 527. For example, in one illustrative arrangement, two bump features 544, 550 are positioned along the outer surface 527 and are preferably positioned 180 degrees apart from one another (both first and second bump features 544, 550 are illustrated in FIG. 19). As illustrated, these bump features 544, 550 may be positioned along the cylindrical extension 516 so that when the dedicated mechanical coupling 514 is fully inserted into the engaging cavity 360 of the dedicated needle assembly 300, the first and second two bump features 544, 550 interact or mate with the first and second recess features 384, 386, respectively. In one preferred arrangement, when a user properly inserts the distal end 504 of the drug delivery device 400 into the needle assembly 300 (FIG. 10), the interaction between the first and second bump features 544, 550 and the first and second recess features 384, 386 will provide a tactile and/or audible confirmation that the two components have been properly connected.

The dedicated mechanical coupling 514 further comprises a first and a second upstand feature 560, 568 located along a second body portion 536 of the cylindrical extension 516 and may extend from the proximal end 524 towards the distal end 530 of the cylindrical extension 516. At a most distal end, first upstand feature 560 comprises a first lip 562 wherein this lip 562 flares radially outward away from the smooth outer surface 527 of the first body portion 526. Second upstand feature 568 comprises a similar lip arrangement 570. As such, the outer most radially directed portions of lips 562, 570 define an outer diameter DOuter 586 that is larger (or wider) than the inner diameter Dinner 518 (see FIG. 19). In a preferred arrangement, this outer diameter DOuter 586 will be larger (or wider) than an inner diameter of a standard "Type A" screw thread needle assembly, such as the outer diameter DType A 620 of the conventional Type A double ended screw thread needle assembly 600 illustrated in FIG. 20. As such, a user will be prevented from attaching a conventional Type A double ended needle assembly onto the dedicated cap 500.

The dedicated mechanical coupling 514 further comprises a first and a second groove 534, 540 positioned 180 degrees apart from each other. Preferably, first groove 534 defines a first width 535 and the second groove 540 defines a second width 541. The first width 535 of the first groove 534 may or may not be equivalent to the second width 541 of the second groove 540. In one preferred arrangement, the first and second widths 535, 541 are generally equivalent.

These groove widths 535, 541 may be generally equivalent to a width of the protrusions provided along the inner wall of the engaging cavity 360. For example, the first width 535 of the first groove 534 may be generally equivalent to the first width 378 of the first protrusion 376. Similarly, the width 541 of the second groove 540 may be generally equivalent to the width 382 of the second protrusion 380 of the dedicated needle assembly 300.

In addition, the dedicated cap 500 may further comprise a first and a second chamfered edge 590, 596 provided near the distal opening of the first groove 534. The second groove 540 comprises a similar chamfer edge arrangement 496, 498. In addition, the dedicated cap 500 comprises an inner surface 578 and on this surface, a connection mechanism 580 in the form of an internal screw thread is provided (illustrated in FIGS. 18 and 19). This screw thread allows the dedicated cap 500 to be threadedly coupled to the conventional threaded distal end of a drug delivery device, such as the device 1 illustrated in FIG. 9. Once connected to the drug delivery device 1, the dedicated cap 500 allows for the interconnection of the device 1 to the dedicated needle assembly 300 in a similar fashion as described herein with respect to the dedicated mechanical coupling as described herein in detail. Once the dedicated cap 500 has been connected to the drug delivery device 1, the device 1 comprises a distal end section adapted and arranged to form a connection of the device 1 to the dedicated needle assembly 300 comprising the dedicated mechanical coupling 310. As those of skill in the art will recognize, alternative temporary and permanent connection mechanisms may also be used.

Exemplary embodiments of the present invention have been described. Those skilled in the art will understand, however, that changes and modifications may be made to these embodiments without departing from the true scope and spirit of the present invention, which is defined by the claims.

REFERENCE NUMERALS

1 Drug delivery device
2 Septum
3 distal end diameter DDE
4 Coupling mechanism/screw thread
5 Cartridge holder
6 Dose setting mechanism/dose button
8 Dose setter
9 Piston rod
10 Medicated module 12 Drug delivery device
13 Thread arrangement
14 Cartridge
16 First medicament
18 Membrane
22 Inner surface of connecting body
24 Connecting body
26 Proximal end
28 Distal end
30 Screw thread/connector
32 First recess
33 External surface of connecting body
34 Second recess
35 Upper surface of connecting body
36 Reservoir
37 Recess
38 Second medicament
40 First needle
42 First piercing end/distal end
44 Second piercing end/proximal end
46 Capsule
48 First pierceable seal/membrane
50 Second pierceable seal/membrane
52 Outer body
54 Distal end of outer body
56 Proximal end of outer body
60 Male member
61 First inner cavity
62 Second inner cavity
63 Inner surface
64 Hub
65 Distal groove
66 Proximal groove
68 Locking feature
70 Biasing member/elastic member
80 Second needle
82 First piercing end/distal end
84 Second piercing end/proximal end
90 Needle guard
96 Arm
98 Arm
110 Proximal direction
120 Distal direction
210 Non-medicated module
212 Drug delivery device
213 Threads
214 Cartridge
216 Medicament
218 Membrane
222 Inner surface of connecting body
224 Connecting body
226 Proximal end
228 Distal end
230 Connector
231 Main stem
239 Recess
245 first recess
261 Inner cavity
263 Inner surface of inner cavity
268 Moveable locking member
270 Biasing member
272a Spring finger, annular spring finger
272b Spring finger, annular spring finger
272c Spring finger, annular spring finger
274 Outer beveled edge/rib
275 Beveled edge of needle guard
280 Double ended needle
282 First piercing end/distal end
284 Second piercing end/proximal end
290 Needle guard
296 Arm
298 Arm
300 Dedicated needle assembly
310 Dedicated mechanical coupling
315 Proximal direction
316 Distal direction
320 Connecting body
322 Cylindrical shape
326 Smooth outer surface
330 Distal end
336 Proximal end
340 Outer surface of connecting body
350 Proximal end surface
360 Engaging cavity
361 Opening
364 First engaging cavity diameter
368 Second engaging cavity diameter
372 Inner wall of engaging cavity
376 First protrusion
378 Width of first protrusion
380 Second protrusion
382 Width of second protrusion
384 First recess feature
386 Second recess feature
400 Dedicated drug delivery device
404 Distal end
408 Distal portion
410 Dedicated cartridge holder
411 Cartridge/ampoule
412 Shoulder
414 Dedicated mechanical coupling
415 Medicament
416 Cylindrical extension
418 Outer diameter of first body portion
424 Proximal end of extension
426 First body portion
427 Outer surface of first body portion
430 Distal end of extension
434 First groove
435 Width of first groove
436 Second body portion
440 Second groove
441 Width of second groove
444 Bump feature
450 Bump feature
460 First upstand feature
462 First lip
468 Second upstand feature
470 Second lip
480 Arrow
486 Inner diameter of first body portion
490 First chamfered edge
496 Second chamfered edge
497 First chamfered edge
498 Second chamfered edge
500 Dedicated cap
502 Main body
504 Distal end
514 Dedicated mechanical coupling
516 Cylindrical extension
518 Inner diameter
524 Proximal end of cylindrical extension
526 First body portion
527 Outer surface of first body portion 530 Distal end of cylindrical extension
534 First groove
535 First width
536 Second body portion
540 Second groove
541 Second width
544 Bump feature
550 Bump feature
560 First upstand feature
562 First lip
568 Second upstand feature
570 Second lip
578 Inner surface
580 Connection mechanism
586 Outer diameter
590 First chamfered edge
596 Second chamfered edge
600 Conventional needle assembly
601 Hub
602 Protrusion
603 Sleeve
604 Thread
605 First end/distal piercing end
606 Double ended needle/cannula
608 Second end/proximal piercing end
620 Conventional Type A diameter

The invention claimed is:

1. A drug delivery system to deliver two or more medicaments, the system comprising:
a multi-use dedicated drug delivery device containing a primary reservoir comprising a plurality of doses of a first medicament and
a single-use medicated module configured to be attached to the dedicated drug delivery device, wherein said medicated module comprises:
a connecting body extending from a distal end to a proximal end;
a proximal needle to pierce a septum of the primary reservoir during attachment of the medicated module to the dedicated drug delivery device and a distal injection needle;
a recess arranged within said connecting body defining a secondary reservoir containing a dose of a second medicament,
wherein the secondary reservoir is located between the proximal needle and the distal needle and is configured for fluid communication with said proximal needle and said distal needle;
a moveable locking member;
a needle guard,
wherein, after delivery of the dose of the second medicament and a dose of the plurality of doses of the first medicament, (i) the moveable locking member is configured to move in a distal direction and lock out the needle guard and (ii) the single-use medicated module is configured to be detached from the dedicated drug delivery device; and
a dedicated mechanical coupling at a proximal end section located at the proximal end of the connecting body for attachment to a distal end section of the dedicated drug delivery device,
wherein the dedicated mechanical coupling defines an engaging cavity which comprises an inner wall and a plurality of protrusions located along said inner wall,
wherein each respective protrusion of said plurality of protrusions is configured to align with and reside in a respective axially extending groove at the distal end section of the dedicated drug delivery device, and
wherein the dedicated mechanical coupling further comprises a plurality of recesses defined along said inner wall,
wherein each respective recess of said plurality of recesses is configured to be axially engaged with a respective bump feature positioned in the distal end section of the dedicated drug delivery device such that said respective bump feature resides in said respective recess.

2. The drug delivery system of claim 1, wherein said dedicated mechanical coupling is configured to prevent a connection of said medicated module to a drug delivery device comprising a screw thread.

3. The drug delivery system according to claim 1, wherein said dedicated mechanical coupling is integral to said medicated module.

4. The drug delivery system according to claim 1, wherein said engaging cavity has a diameter that is configured to define a width that is less than a diameter of a conventional Type A needle assembly according to EN ISO 11608-2:200.

5. The drug delivery system according to claim 1, wherein said medicated module comprises:
an outer body operatively coupled to said connecting body,
wherein the needle guard is operatively coupled to said outer body, the needle guard being adapted and arranged to provide protection of the distal needle, wherein the needle guard is movable in a proximal direction during an injection step,
a biasing element positioned between said outer body and said needle guard,
the biasing element being configured to exert an axially directed force onto the needle guard.

6. The drug delivery system according to claim 1, wherein the proximal needle is rigidly affixed in an upper surface of the connecting body and wherein the medicated module comprises an outer body hub element, the distal needle being rigidly affixed in said outer body hub element.

7. A drug delivery system to deliver two or more medicaments, the system comprising:
a dedicated drug delivery device containing a primary reservoir comprising a plurality of doses of a first medicament, the dedicated drug delivery device having a proximal end and a distal end, wherein the dedicated drug delivery device comprises a plurality of axially extending grooves at a distal end section located at the distal end; and
a single-use medicated module configured to be attached to the dedicated drug delivery device, wherein said medicated module comprises:
a connecting body extending from a distal end to a proximal end;
an outer body slidably engaged with the connecting body;
a proximal needle rigidly affixed to the connecting body to pierce a septum of the primary reservoir during attachment of a proximal end of the medicated module to the distal end section of the dedicated drug delivery device and a distal injection needle rigidly affixed to the outer body;
a recess arranged within said connecting body defining a secondary reservoir containing a dose of a second medicament, wherein the secondary reservoir is located between the proximal needle and the distal needle and is configured for fluid communication with said proximal needle and said distal needle;

a moveable locking member;

a needle guard, wherein, after delivery of the dose of the second medicament and a dose of the plurality of doses of the first medicament, (i) the moveable locking member is configured to move in a distal direction and lock out the needle guard and (ii) the single-use medicated module is configured to be detached from the dedicated drug delivery device; and a dedicated mechanical coupling at a proximal end section located at the proximal end of the connecting body for attachment to the distal end section of the dedicated drug delivery device, wherein the dedicated mechanical coupling defines an engaging cavity which comprises an inner wall and a plurality of protrusions located along said inner wall, wherein each respective protrusion of said plurality of protrusions is configured to align with and reside in a respective axially extending groove of the plurality of axially extending grooves, and where the dedicated mechanical coupling further comprises a plurality of recesses defined along said inner wall, wherein each respective recess of said plurality of recesses is configured to be axially engaged with a respective bump feature positioned in the distal end section of the dedicated drug delivery device such that said respective bump feature resides in said respective recess.

8. The drug delivery system of claim 7, wherein the medicated module is configured to be releasably attached to the dedicated drug delivery device such that the medicated module and the dedicated drug delivery device are fully detachable from one another.

9. The drug delivery system of claim 7, wherein the outer body is slidable relative to the connecting body in a proximal direction from an initial position to a dose injecting position.

10. The drug delivery system of claim 9, wherein proximal movement of the outer body from the initial position to the dose injecting position causes a distal end of the proximal needle to penetrate a proximal pierceable seal of the secondary reservoir.

11. The drug delivery system of claim 10, wherein proximal movement of the outer body from the initial position to the dose injecting position causes a proximal end of the distal needle to penetrate a distal pierceable seal of the secondary reservoir.

* * * * *